(12) United States Patent
Hirose et al.

(10) Patent No.: US 9,791,090 B2
(45) Date of Patent: Oct. 17, 2017

(54) IN-PIPE MOVING APPARATUS

(71) Applicant: HiBot Corp., Tokyo (JP)

(72) Inventors: Shigeo Hirose, Tokyo (JP); Michele Guarnieri, Tokyo (JP); Paulo Debenest, Tokyo (JP)

(73) Assignee: HiBot Corp., Tokyo (JP)

(*) Notice: Subject to any disclaimer, the term of this patent is extended or adjusted under 35 U.S.C. 154(b) by 0 days.

(21) Appl. No.: 14/891,670

(22) PCT Filed: Jul. 4, 2014

(86) PCT No.: PCT/JP2014/067947
§ 371 (c)(1),
(2) Date: Nov. 16, 2015

(87) PCT Pub. No.: WO2015/012087
PCT Pub. Date: Jan. 29, 2015

(65) Prior Publication Data
US 2016/0123517 A1    May 5, 2016

(30) Foreign Application Priority Data

Jul. 26, 2013  (JP) ................................. 2013-155720

(51) Int. Cl.
*F16L 55/40*      (2006.01)
*B61B 13/10*      (2006.01)
(Continued)

(52) U.S. Cl.
CPC ............ *F16L 55/40* (2013.01); *B60K 7/0007* (2013.01); *B61B 13/10* (2013.01); *F16L 55/32* (2013.01);
(Continued)

(58) Field of Classification Search
CPC .................. F16L 55/40; B61B 13/10
(Continued)

(56) References Cited

U.S. PATENT DOCUMENTS 4,862,808 A * 9/1989 Hedgcoxe ................ B25J 5/007
                                                    104/138.2
5,172,639 A * 12/1992 Wiesman ................ F16L 55/28
                                                    104/138.2
(Continued)

FOREIGN PATENT DOCUMENTS

JP      04-008658 A     1/1992
JP      H08-133073 A    5/1996
(Continued)

OTHER PUBLICATIONS

Edwin Dertien, Stefano Stramigioli, Kees Pulles, "Development of an inspection robot for small diameter gas distribution mains", 2011 IEEE International Conference on Robotics and Automation, pp. 5044-5049, Shanghai International Conference Center May 9-13, 2011.

(Continued)

*Primary Examiner* — Jason C Smith
(74) *Attorney, Agent, or Firm* — Masuvalley & Partners

(57) ABSTRACT

An in-pipe moving apparatus for passing through a pipe bent in any direction without control of the attitude of the apparatus is provided. The in-pipe moving apparatus may include at least three sets of tire-integrated wheel units arranged in series in a traveling direction and at least two sets of joint sections that pivotably link the at least three sets of tire-integrated wheel units to each other. Each of the at least three sets of tire-integrated wheel units includes a tire-integrated wheel, a drive section, a first frame fixed to the drive section, and at least one second frame pivotably attached to the drive section. A bending generator is provided between one of the first frames and one of the second frames in the at least three sets of tire-integrated wheel units and imparts tension for causing the first frames and the second frames to have a V-like bent shape.

3 Claims, 28 Drawing Sheets

(51) Int. Cl.
*F16L 55/32* (2006.01)
*B60K 7/00* (2006.01)
*G01N 21/954* (2006.01)
*F16L 101/10* (2006.01)
*F16L 101/30* (2006.01)

(52) U.S. Cl.
CPC ............... *B60K 2007/0038* (2013.01); *B60K 2007/0092* (2013.01); *B60Y 2200/60* (2013.01); *F16L 2101/10* (2013.01); *F16L 2101/30* (2013.01); *G01N 21/954* (2013.01)

(58) Field of Classification Search
USPC ............................................ 104/138.2, 138.1
See application file for complete search history.

(56) References Cited

U.S. PATENT DOCUMENTS

| | | | | |
|---|---|---|---|---|
| 5,371,363 A * | 12/1994 | Lilimpakis | ............... | G01T 1/169 104/138.2 |
| 5,878,783 A * | 3/1999 | Smart | ............... | F16L 55/28 104/138.2 |
| 5,971,404 A * | 10/1999 | Stoves | ............... | F16L 55/44 104/138.2 |
| 6,019,048 A * | 2/2000 | Seeberger | ............... | F16L 55/28 104/138.2 |
| 6,035,786 A * | 3/2000 | McKay | ............... | F16L 55/28 104/138.1 |
| 6,123,027 A * | 9/2000 | Suyama | ............... | F16L 55/28 104/138.2 |
| 6,339,993 B1 * | 1/2002 | Comello | ............... | F16L 55/28 104/138.2 |
| 6,450,104 B1 * | 9/2002 | Grant | ............... | B08B 9/049 104/138.1 |
| 7,954,575 B1 * | 6/2011 | Bloxsom | ............... | H02G 1/088 104/138.1 |
| 8,402,911 B1 * | 3/2013 | Weisenberg | ............... | F16L 55/265 104/138.2 |
| 2007/0151475 A1 * | 7/2007 | Nicholson | ............... | B08B 9/035 104/138.2 |
| 2008/0115606 A1 * | 5/2008 | Suzuki | ............... | A61B 1/00147 74/111 |
| 2008/0245258 A1 * | 10/2008 | Herron | ............... | F16L 55/32 104/138.2 |
| 2011/0011299 A1 * | 1/2011 | Beck | ............... | B60B 19/003 104/138.2 |
| 2011/0073001 A1 * | 3/2011 | Louis | ............... | F16L 55/28 104/138.2 |
| 2014/0165870 A1 * | 6/2014 | Bichler | ............... | E03F 3/06 104/138.2 |
| 2015/0107485 A1 * | 4/2015 | Hirose | ............... | B61B 13/10 105/3 |
| 2015/0330551 A1 * | 11/2015 | Van Nie | ............... | G01N 29/225 138/98 |
| 2016/0123517 A1 * | 5/2016 | Hirose | ............... | B61B 13/10 105/3 |
| 2016/0256903 A1 * | 9/2016 | Motzo | ............... | B05B 13/0436 |

FOREIGN PATENT DOCUMENTS

| | | |
|---|---|---|
| JP | H08-230666 A | 9/1996 |
| JP | 2005-241474 A | 9/2005 |
| JP | 2012-076475 A | 4/2012 |

OTHER PUBLICATIONS

Yuji Shimizu, ISA/JP, International Search Report dated Oct. 28, 2014 in International Patent Application No. PCT/JP2014/067947, 3 pages with English translation.

* cited by examiner

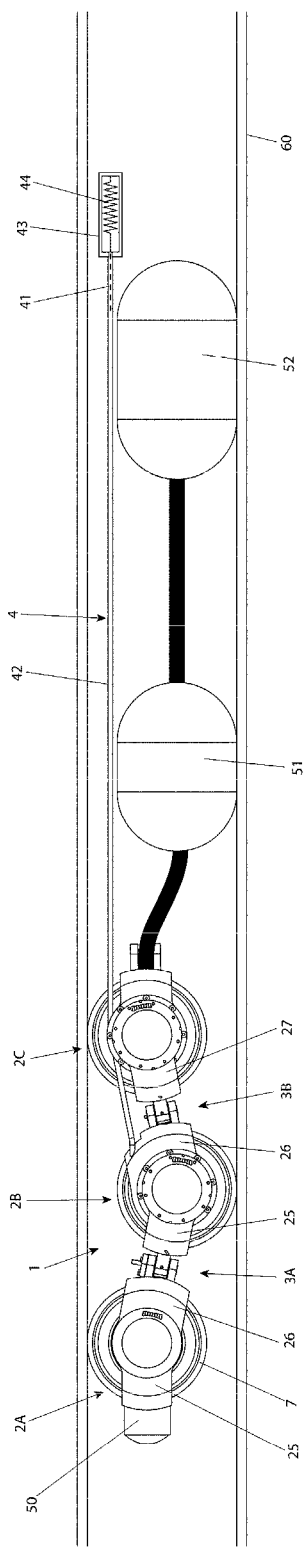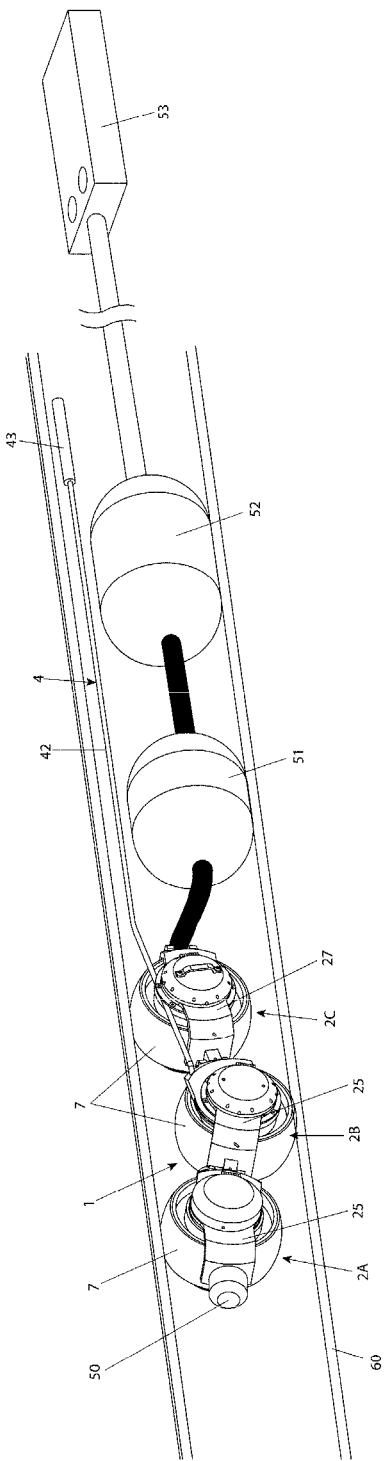

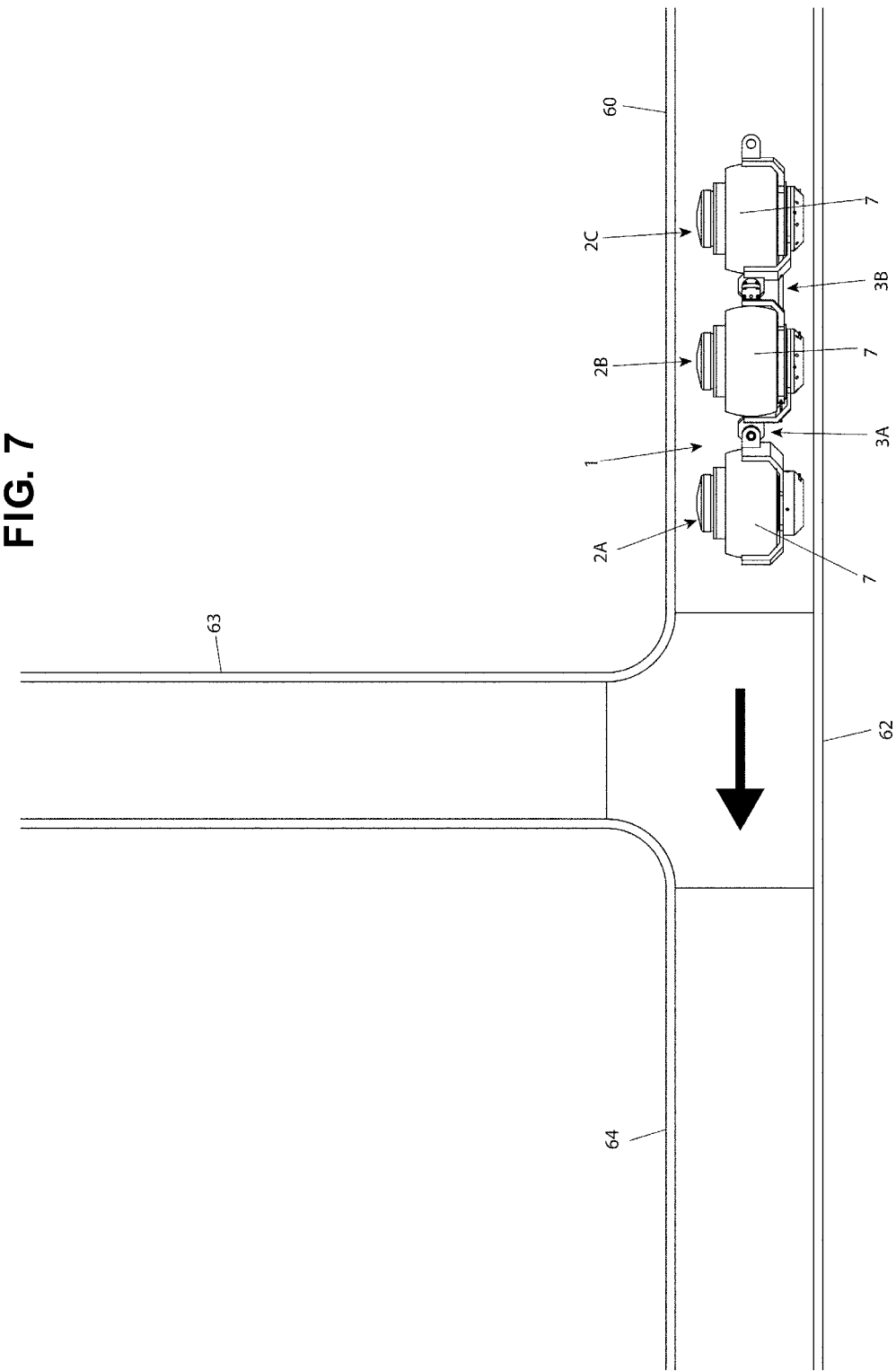

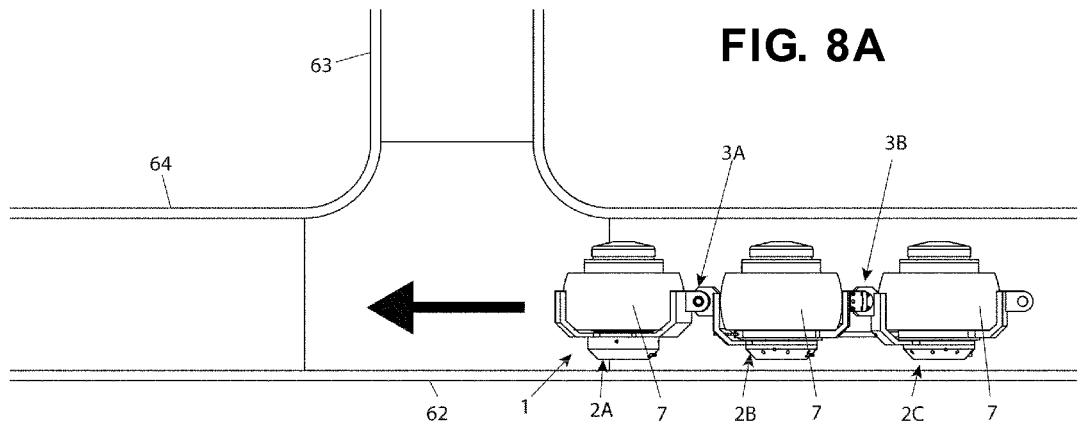
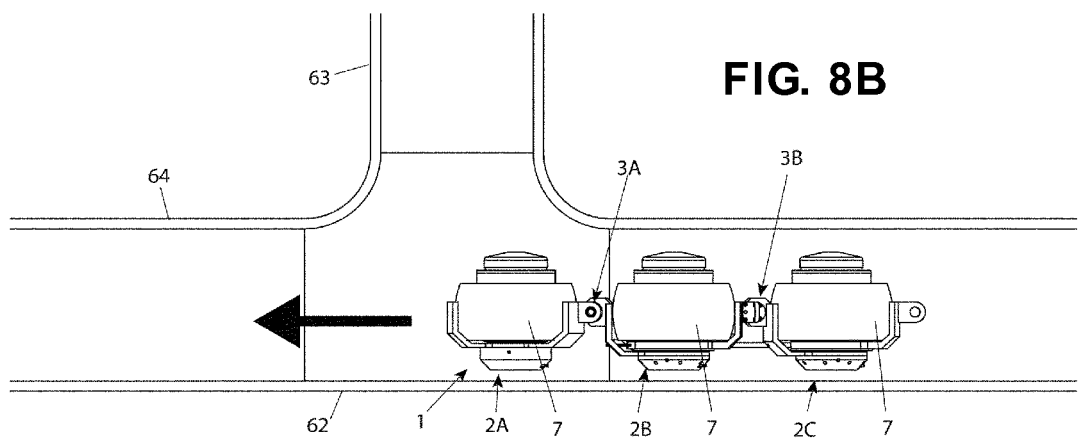
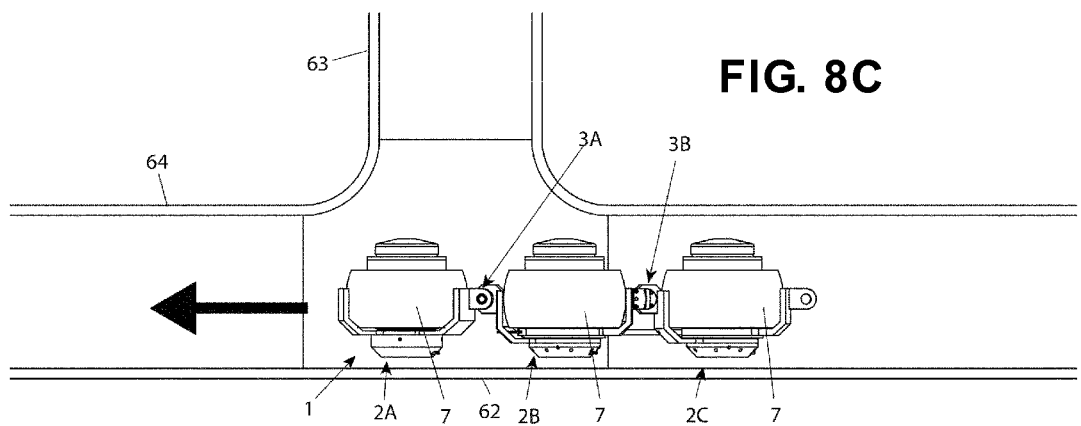

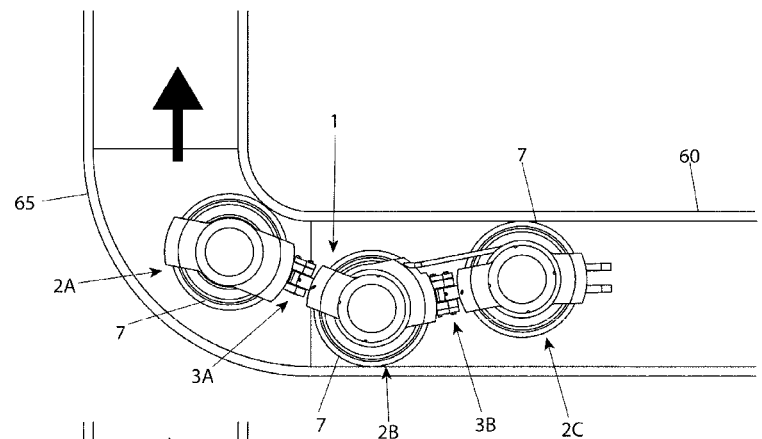
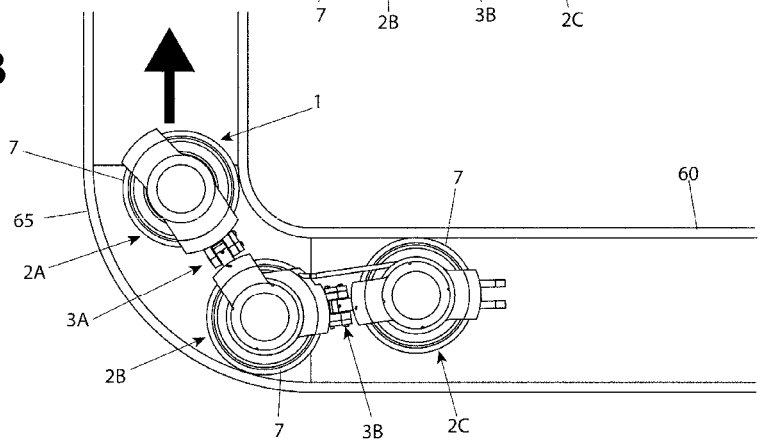
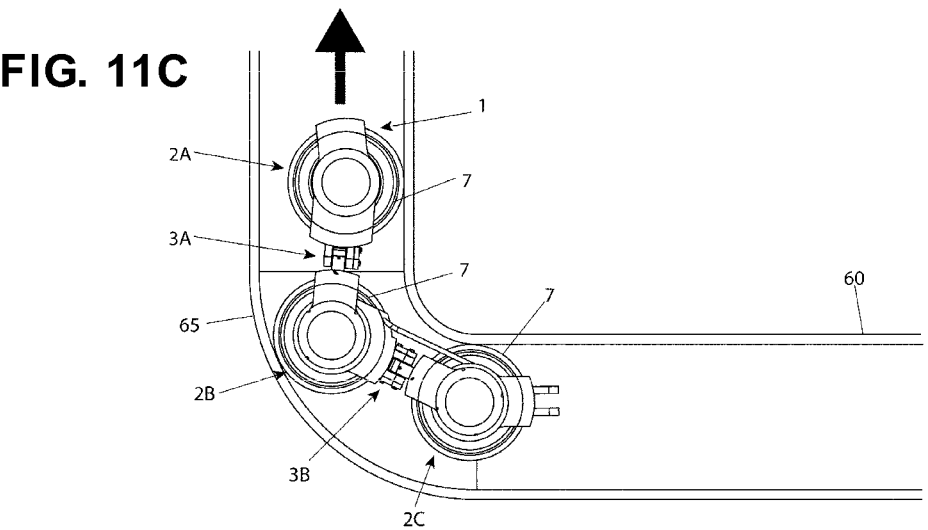

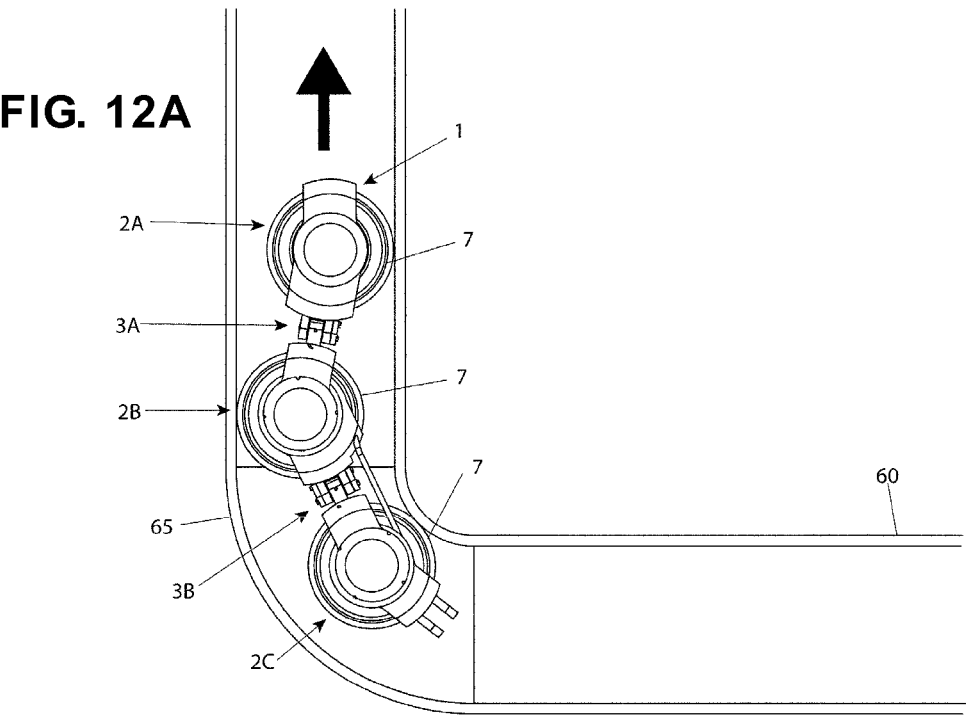
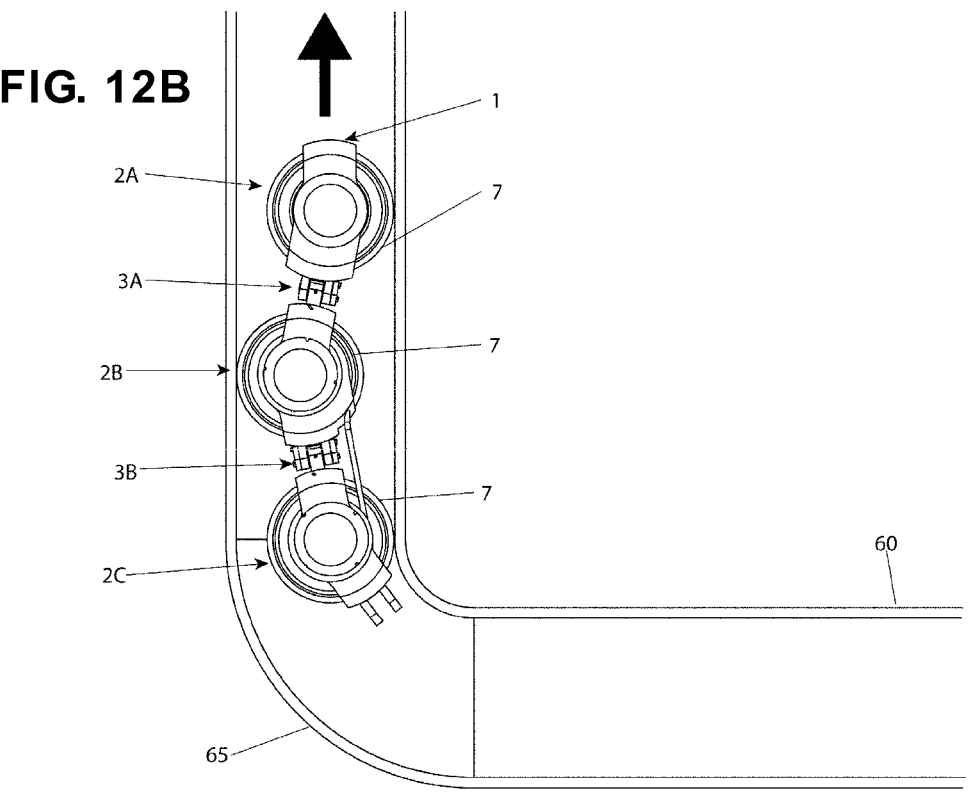

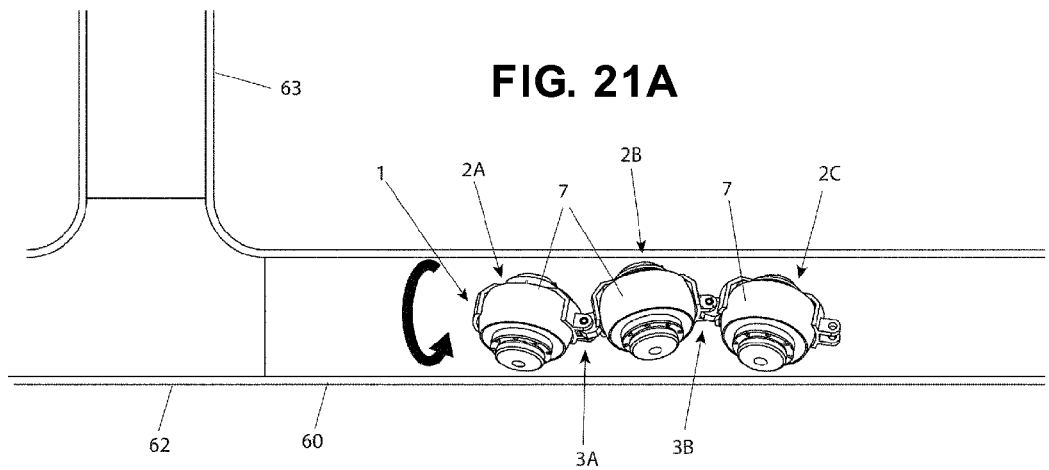
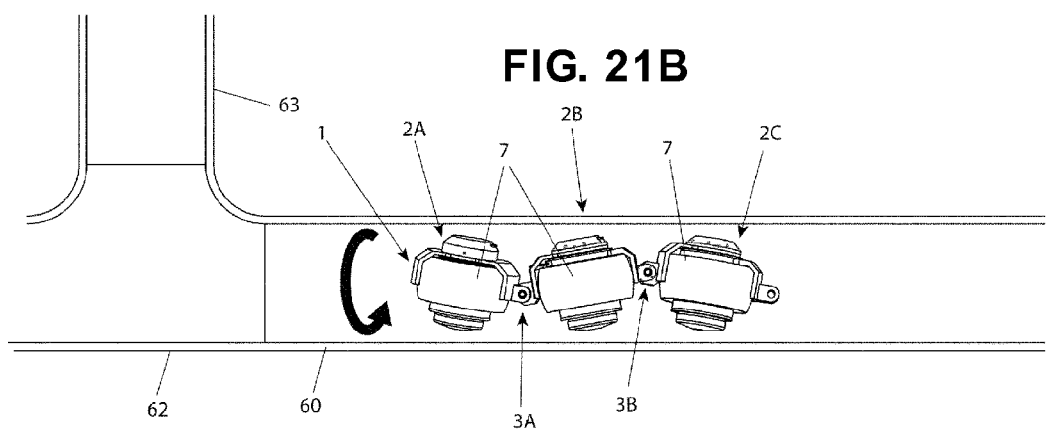
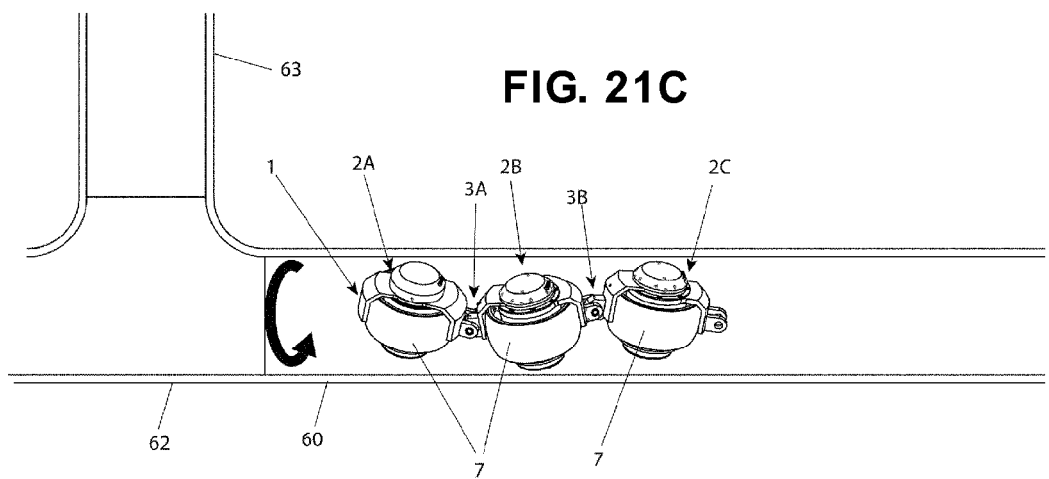

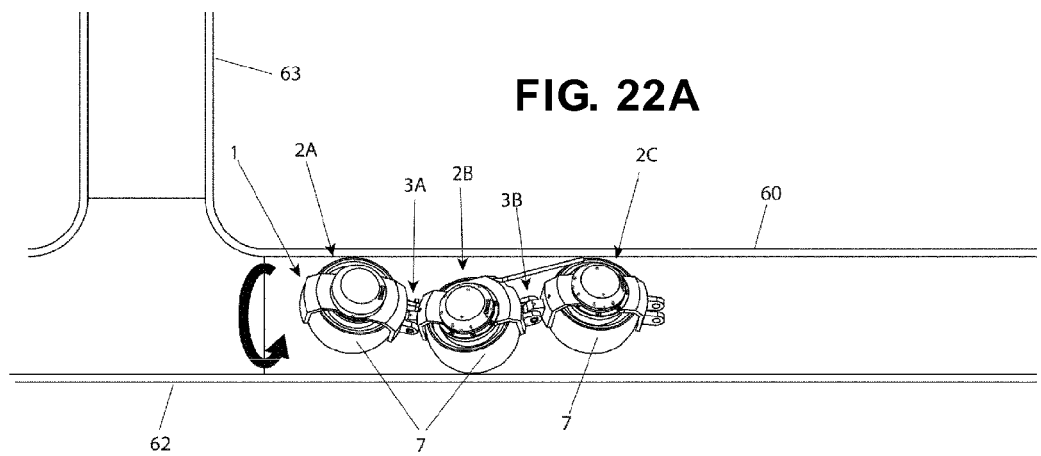
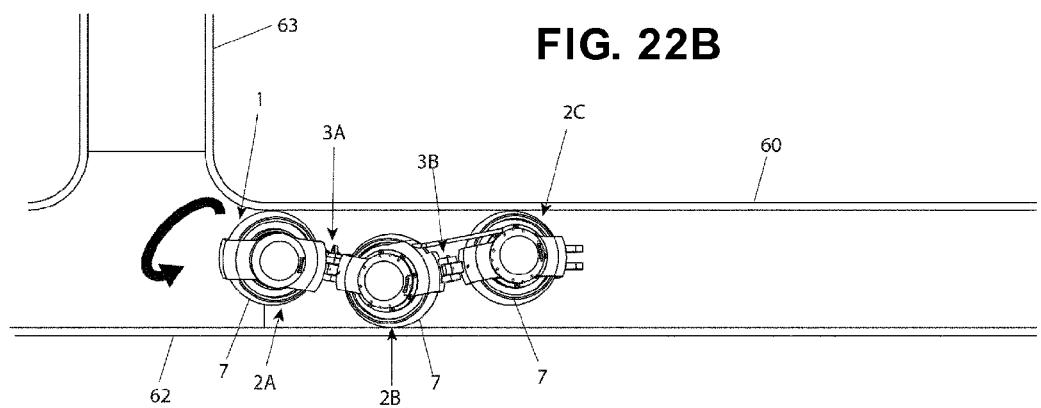
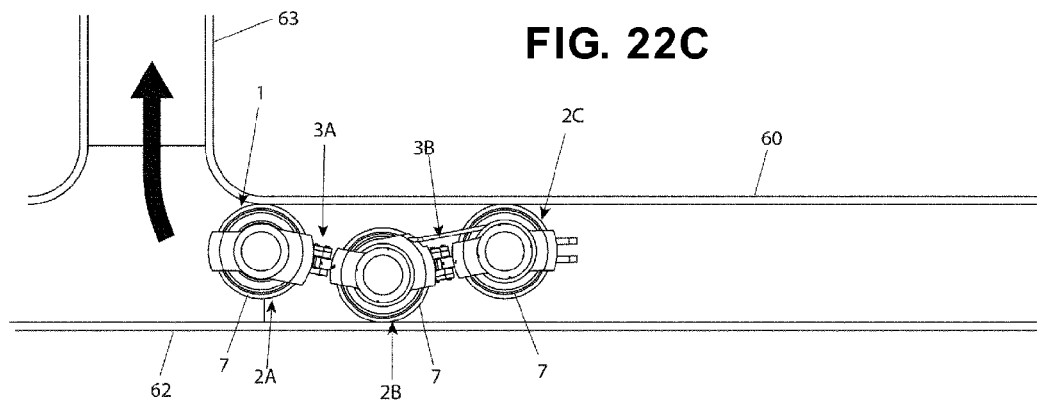

IN-PIPE MOVING APPARATUS

This application is the U.S. National Phase of International Application No. PCT/JP2014/067947 filed on Jul. 4, 2014, entitled "Apparatus Moving Through Interior Of Pipe," and claims priority to Japanese Patent Application No. 2013-155720, filed on Jul. 26, 2013, which are hereby expressly incorporated by reference in their entirety for all purposes.

TECHNICAL FIELD

The present invention relates to an in-pipe moving apparatus capable of freely moving through a pipe having a bent segment and a bifurcating segment and further capable of transporting a work device for inspecting and repairing the inside of the pipe.

BACKGROUND OF THE DISCLOSURE

There is in general a great demand for a technology that allows inspection and repair of the inside of a pipe, such as a gas pipe, a water supply pipe, a sewer pipe, and other public facility pipes, and pipes in a chemical plant, without cutting operation of the pipe. To achieve this, it is necessary to insert a work device into a pipe through an opening thereof and provide an in-pipe moving apparatus capable of moving through a bent segment and a bifurcating segment of the pipe and transporting the work device to a desired position.

PTL 1, PTL 2, PTL 3, and NPTL 1 describe examples of an apparatus of related art for inspecting the inside of a pipe while moving through the pipe.

CITATION LIST

Patent Literature

PTL 1: Japanese Patent Laid-Open No. 2012-76475 (Japanese Patent No. 4,677,595)
PTL 2: Japanese Patent Laid-Open No. 2005-241474
PTL 3: Japanese Patent Laid-Open No. H8-230666

Non-Patent Literature

NPTL 1: Edwin Dertien, Stefano Stramigioli, Kees Pulles, "Development of an inspection robot for small diameter gas distribution mains", 2011 IEEE International Conference on Robotics and Automation, pp. 5044-5049, Shanghai International Conference Center May 9-13, 2011

SUMMARY OF THE INVENTION

Technical Problem

PTL1 has been filed as a patent application previously by the inventors of the invention of the present application and describes a pipe inspection apparatus capable of moving in a desired direction in a bent pipe, a bifurcating pipe, and pipes having other forms. The pipe inspection apparatus according to the PTL 1 includes at least one drive unit and at least one inspection unit. The drive unit has a plurality of drive sections, a plurality of linkage sections that link the drive sections with each other, two manipulation cables that pass through the drive sections and the linkage sections, and a tension adjustment section that adjusts the tension of each of the manipulation cables, and each of the drive sections has an axle that can be rotated with a motor and a tire-integrated wheel attached to the axle. In the configuration described above, when the two manipulation cables are pulled with the same magnitude of tension, the drive unit bends in a zigzag shape and moves straight with the tire-integrated wheels of the drive sections being in contact with the inner wall of the pipe. On the other hand, when the two manipulation cables are pulled with different magnitudes of tension, the drive unit bends in a helically zigzag shape and travels along a helical path with the tire-integrated wheels of the drive sections being in contact with the inner wall of the pipe.

Document 2 describes an apparatus that inspects the inside of a bent pipe having a small inner diameter. The pipe inspection apparatus according to PTL2 is characterized in that it includes a plurality of tire-integrated wheels and a mechanism that produces pushing force that separates the line that connects two of the plurality of tire-integrated wheels from another one of the plurality of tire-integrated wheels.

PTL 3 describes an apparatus capable of traveling through a pipe having a changing diameter and a pipe having a foreign body, a step, and an elbow in a stable attitude while keeping pushing the inner wall of the pipe at fixed pressure. The in-pipe traveling apparatus according to PTL 3 is an in-pipe traveling apparatus that inspects the inner surface of an underground pipe, an aboveground, highly elevated pipe, and other pipes that do not allow entry of an operator and therefore prevent regular interior inspection. The apparatus is characterized in that the apparatus includes two traveling tire-integrated wheel sets each of which is formed of a group of a plurality of tire-integrated wheels and which are extendable and contractable in opposite directions in a cross section of the pipe, a force transmission mechanism that pushes the two sets of traveling tire-integrated wheels with fixed pushing force in the direction from the pipe axis toward the pipe wall, and a traveling mechanism that simultaneously drives all the tire-integrated wheels of the two sets of traveling tire-integrated wheels, and the apparatus is further characterized in that it is remotely so operated as to be capable of freely moving through the pipe.

NPTL 1 describes a compact pipe inspection robot capable of moving through an extremely narrow pipe. The pipe inspection robot according to NPTL1 is aimed at autonomously inspecting a specific region of a gas distribution network and recording a correct position of a pipe and the state thereof.

In any of the apparatus described in PTL1, PTL2, PTL3, and NPTL 1, however, a large number of parts are used and the structure is therefore complicated, resulting in a complicated control mechanism for causing the apparatus to travel. Further, to allow the apparatus to pass through a bent segment, it is necessary to control the attitude of the apparatus around the axis thereof before the apparatus enters the bent segment, specifically, in a position upstream of the bent segment by a predetermined distance. Therefore, to allow the apparatus to pass a pipe having a large number of bent segments, it is necessary to manipulate the apparatus while monitoring the bending direction of the pipe with a plurality of small cameras mounted on the apparatus, which makes the manipulation of the apparatus extremely difficult.

For example, in the apparatus according to PTL 1, to allow the drive unit to pass through a pipe structure having a horizontal segment bent in an L-like shape and a vertical linear segment extending in the vertical direction from an intermediate linear segment on one side of the horizontal segment, it is necessary to cause the pipe inspection apparatus to pivot around the axis of the pipe to align the direction in which the pipe inspection apparatus is bent in a zigzag shape with the direction of bending of each pipe segment. However, since a bent pipe segment does not allow the pivotal motion, it is necessary to perform the pivotal motion in a situation where one drive unit has entirely entered the intermediate linear segment. The in-pipe inspection apparatus is therefore undesirably not allowed to move when the length of the apparatus is longer than the intermediate linear segment of the pipe. Further, even when the length of the pipe inspection apparatus is shorter than the intermediate linear segment, a short distance for the pivotal motion undesirably requires the apparatus to repeat reciprocating motion many times for the pivotal motion.

Further, in the apparatus according to PTL 1, the following two types of action is achieved: pulling the pair of manipulation cables to bend the apparatus in a zigzag shape; and bending the apparatus in a zigzag shape in the direction perpendicular to the zigzag bending described above to push the helically arranged tire-integrated wheels against the inner wall of the pipe. A large magnitude of frictional force is therefore produced between each of the cables and a tube that guides the cable when the apparatus passes through each joint, undesirably resulting in unsmooth zigzag bending motion.

The apparatus according to PTL 2 has a structure in which a pair of tire-integrated wheels disposed on the front and rear sides of a main body of the apparatus are each supported by an arm swingably only in two directions (upward and downward directions, for example), and no swing motion is allowed in the direction perpendicular to the two directions. No pivotal motion can therefore be performed in a pipe (no rotation around the axis of the pipe can be performed), and the apparatus is therefore not allowed to move through a pipe having segments bent in a variety of directions.

The apparatus according to PTL 3 has a structure that allows the apparatus to travel through a pipe with the plurality of tire-integrated wheels pushed out at fixed pressure in two directions against the inner surface of the pipe. This structure allows a stable attitude of the apparatus to be ensured but requires complicated control to allow the apparatus to pivot in the pipe, as in the case of the apparatus according to PTL 2, resulting in a problem of difficulty in smoothly moving through a bent segment and a bifurcating segment of the pipe.

The apparatus according to NPTL 1 is capable of moving through a pipe having segments bent in a variety of directions because a central section of the apparatus has in principle flexibility of rotation around the axis of the pipe. However, to allow an operator at a location outside the pipe to remotely operate the apparatus, it is necessary to monitor and determine each bending direction of the pipe with a large number of small cameras mounted on the apparatus and correct the attitude of the apparatus to be aligned with the bending direction for each of the bending segments, resulting in extreme difficulty in operation.

The invention has been made in view of the problems described above in related art, and an object of the invention is to provide an in-pipe moving apparatus that has an extremely simple structure, readily achieves dustproof and waterproof capabilities, is capable of passing through a bent segment and other nonlinear segments of a pipe bent in any direction without control of the attitude of the apparatus, and is characterized by selectivity of a traveling direction in a T-shaped bifurcating pipe.

Solution to Problem

An in-pipe moving apparatus according to the invention is characterized in that it includes at least three sets of tire-integrated wheel units arranged in series in a traveling direction and at least two sets of joint sections that pivotably link the at least three sets of tire-integrated wheel units to each other, each of the at least three sets of tire-integrated wheel units includes a tire-integrated wheel, a drive section that drives and rotates the tire-integrated wheel, a first frame fixed to the drive section, and at least one second frame pivotably attached to the drive section, a bending generator is provided between one of the first frames and one of the second frames in the at least three sets of tire-integrated wheel units and imparts tension for causing the first frames and the second frames to have a V-like bent shape, and each of the two sets of joint sections is configured to be pivotable in a direction roughly perpendicular to the direction in which the second frames pivot.

The first frame in the tire-integrated wheel unit located in an intermediate position among the at least three sets of tire-integrated wheel units may be pivotably linked to the second frame in an adjacent tire-integrated wheel unit, and the second frame in the intermediate tire-integrated wheel unit may be pivotably linked to the first frame in an adjacent tire-integrated wheel frame to configure the at least two sets of joint sections.

The tire-integrated wheel units may be so configured as to each include a prime mover, the tire-integrated wheel pivotably linked to an output section of the prime mover on a radially outward side of the output section with a predetermined gap between the tire-integrated wheel and the output section and integrated with the output section of the prime mover, the first frame fixed to a member of the prime mover, and the second frame supported pivotably relative to the member of the prime mover, and further include the bending generator that imparts tension for causing the first frames and the second frames to have a V-like bent shape.

The bending generator can be formed of a spring that produces force that causes the first frames and the second frames to approach each other, a spring having a cable that produces the force, or a tension adjustment mechanism that changes tension produced by a spring that produces the force.

Advantageous Effects of Inventions

The in-pipe moving apparatus according to the invention has an extremely simple structure, readily achieves dustproof and waterproof capabilities, is capable of passing through a bent segment and other nonlinear segments of a pipe bent in any direction without control of the attitude of the apparatus, and is characterized by selectivity of a traveling direction in a T-shaped bifurcating pipe.

BRIEF DESCRIPTION OF DRAWINGS

FIGS. 6A and 6B describe a state in which the in-pipe moving apparatus to which an inspection device and other devices are connected is caused to move through a pipe, FIG. 6A being a side view and FIG. 6B being a perspective view viewed from the front in the traveling direction.

FIG. 7 describes action of the in-pipe moving apparatus shown in FIG. 1 that has a vertical attitude and moves straight through a T junction of a pipe and is a plan view of a state immediately before the in-pipe moving apparatus enter the T junction.

FIGS. 8A to 8C describe the action of the in-pipe moving apparatus shown in FIG. 1 that has a vertical attitude and moves straight through a T junction of a pipe, FIG. 8A being a plan view of a state immediately before the tire-integrated wheel of the first (front) tire-integrated wheel unit enters the T junction, FIG. 8B being a plan view of a state in which the tire-integrated wheel of the first tire-integrated wheel unit has entered the T junction, and FIG. 8C being a plan view of a state in which the tire-integrated wheel of a second tire-integrated wheel unit has entered the T junction.

FIGS. 11A to 11C describe the action of the in-pipe moving apparatus shown in FIG. 1 that has a horizontal attitude and moves through an L-shaped curve of a pipe, FIG. 11A being a plan view of a state in which the second tire-integrated wheel unit has moved to a point immediately before the L-shaped curve with the tire-integrated wheel in contact with the outer-side inner wall surface of the pipe, FIG. 11B being a plan view of a state in which the second tire-integrated wheel unit has entered the L-shaped curve with the tire-integrated wheel in contact with the outer-side inner wall surface of the pipe, and FIG. 11C being a plan view of a state in which the third tire-integrated wheel unit has entered the L-shaped curve with the tire-integrated wheel in contact with the inner-side inner wall surface of the pipe.

FIGS. 12A and 12B describe the action of the in-pipe moving apparatus shown in FIG. 1 that has a horizontal attitude and moves through an L-shaped curve of a pipe, FIG. 12A being a plan view of a state in which the third tire-integrated wheel unit passes through the L-shaped curve with the tire-integrated wheel in contact with the inner-side inner wall surface of the pipe, and FIG. 12B being a plan view of a state immediately after the third tire-integrated wheel unit has passed through the L-shaped curve with the tire-integrated wheel in contact with the inner-side inner wall surface of the pipe.

FIGS. 21A to 21C describe the attitude control action of the in-pipe moving apparatus according to the first embodiment of the invention, FIG. 21A is a plan view of a state in which the attitude is rotated by about 60 degrees from the state in FIG. 20A, FIG. 21B is a plan view of a state in which the attitude is rotated by about 90 degrees from the state in FIG. 20A, and FIG. 21C is a plan view of a state in which the attitude is rotated by about 120 degrees from the state in FIG. 20A.

FIGS. 22A to 22C describe the attitude control action of the in-pipe moving apparatus according to the first embodiment of the invention, FIG. 22A is a plan view of a state in which the attitude is rotated by about 150 degrees from the state in FIG. 20A, FIG. 22B is a plan view of a state in which the attitude is rotated by about 180 degrees from the state in FIG. 20A, and FIG. 22C is a plan view of a state in which the attitude of the tire-integrated wheels of the three sets of tire-integrated wheel units have changed to a horizontal attitude after the state in FIG. 22B.

BRIEF DESCRIPTION OF THE INVENTION

Embodiments of an in-pipe moving apparatus according to the invention will be described below with reference to FIGS. 1 to 28A and 28B.

A first embodiment of the in-pipe moving apparatus according to the invention will first be described below with reference to FIGS. 1 to 24A and 24B.

An in-pipe moving apparatus 1 according to the first embodiment of the invention includes three sets of tire-integrated wheel units 2A, 2B, and 2C, two sets of joint sections 3A and 3B, which pivotably connect the adjacent tire-integrated wheel units 2A and 2B to each other and the adjacent tire-integrated wheel units 2B and 2C to each other, a bending generator 4, which imparts tension for achieving a V-shaped bent arrangement of the three sets of tire-integrated wheel units 2A to 2C disposed in series, and other components, as shown in FIGS. 1 to 5.

Figure 3:
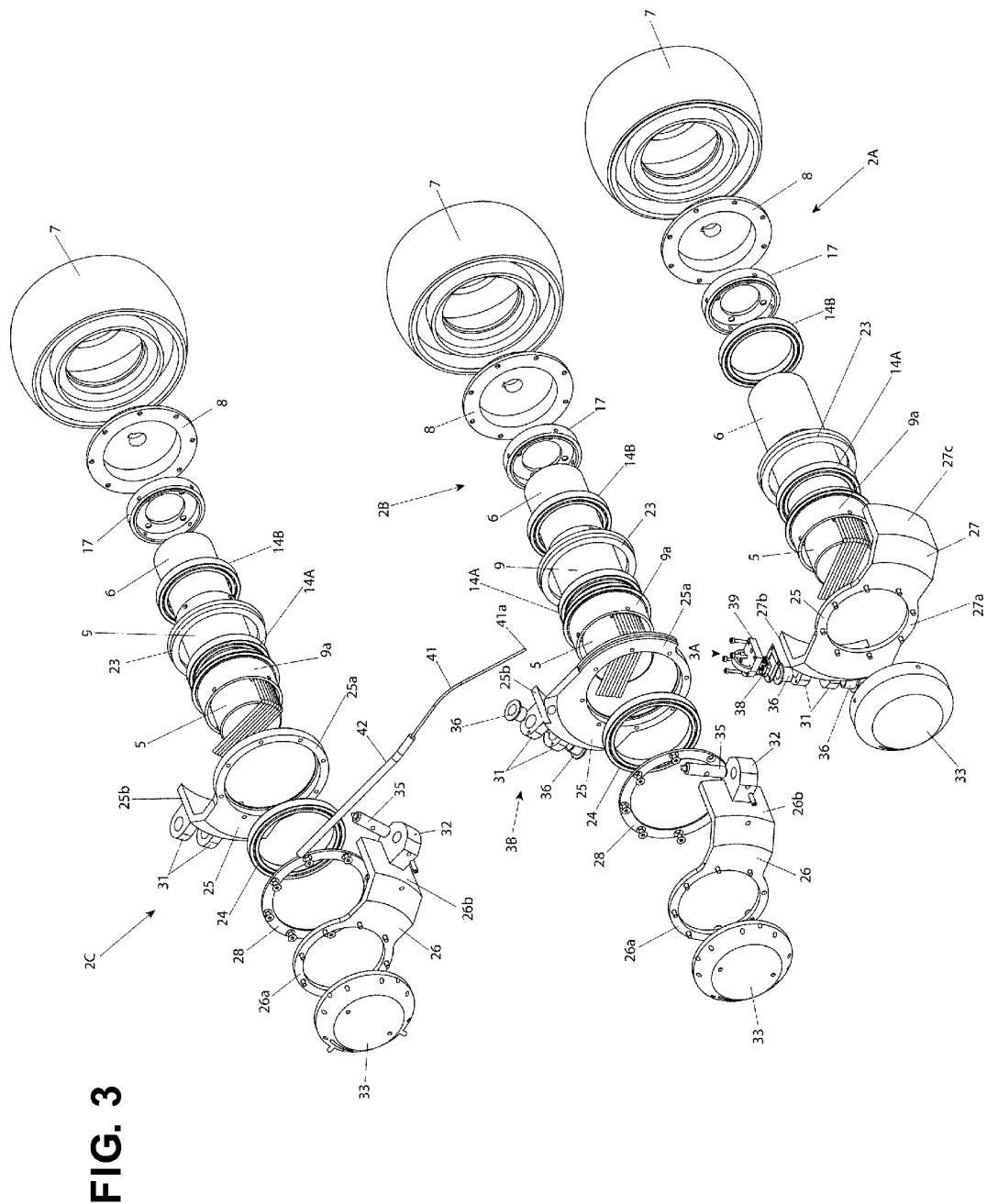
FIG. 3 is an exploded perspective view of the in-pipe moving apparatus shown in FIG. 1.
Figure 4:
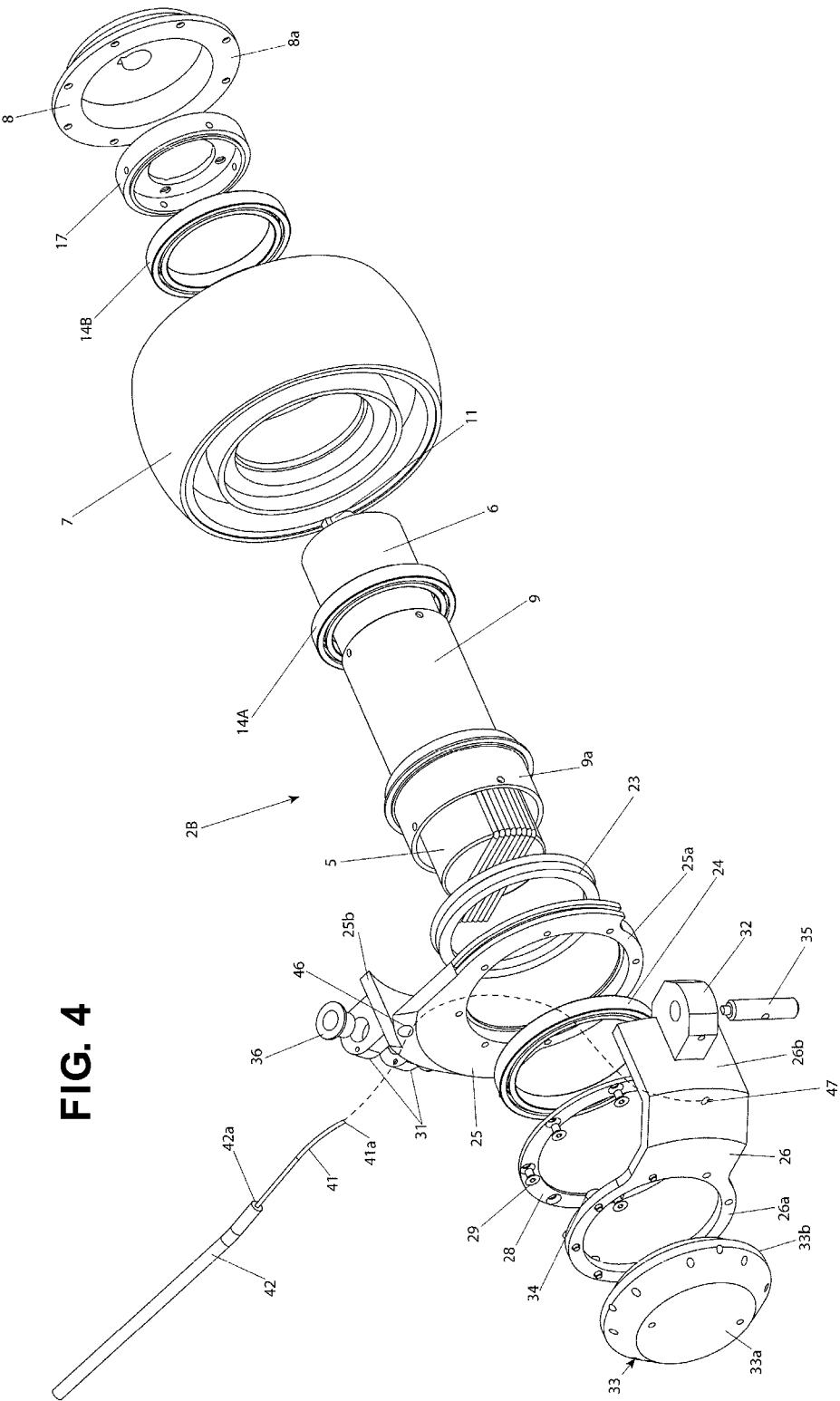
FIG. 4 is an exploded perspective view of one of tire-integrated wheel units that form the in-pipe moving apparatus shown in FIG. 1.
Figure 5:
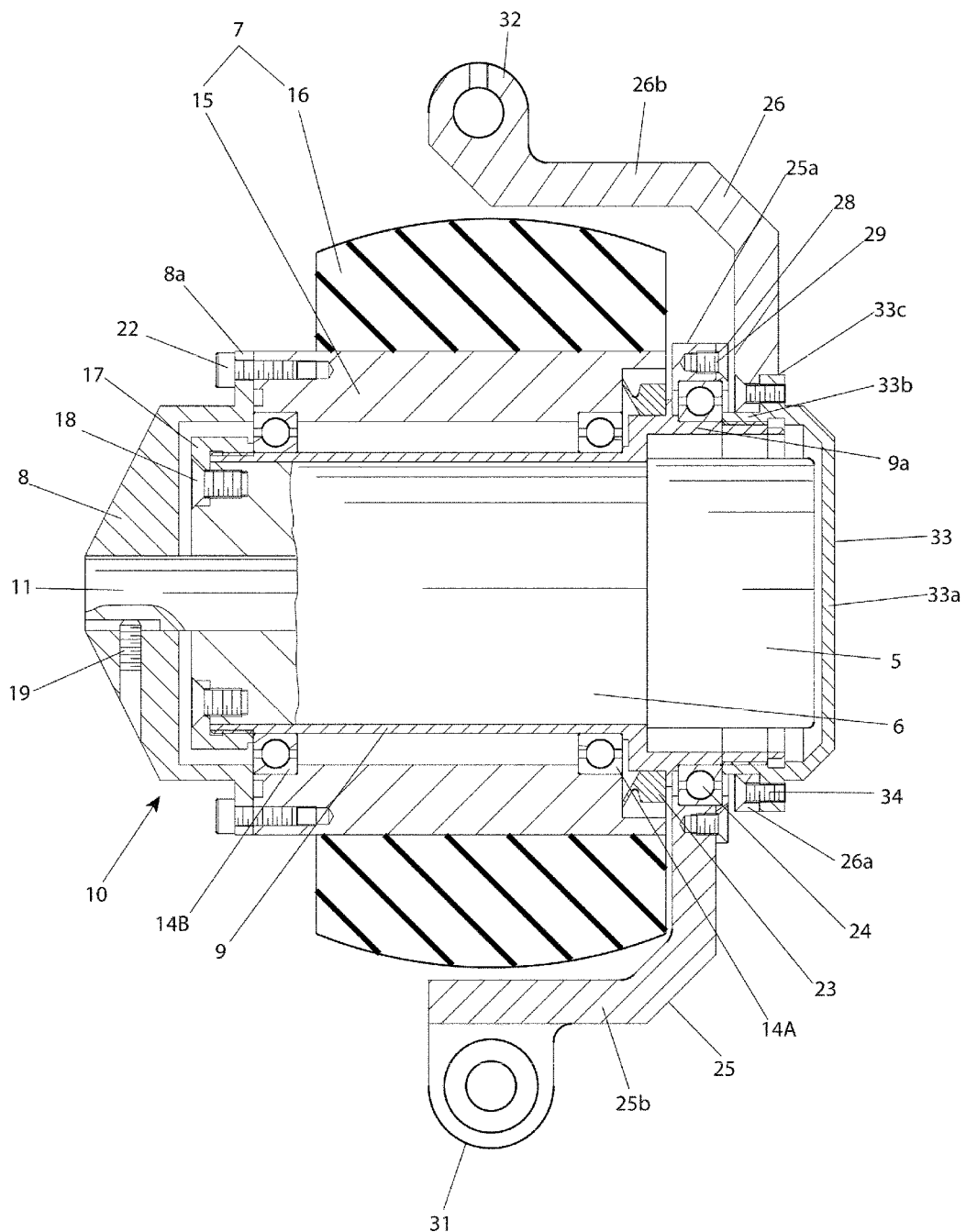
FIG. 5 is a cross-sectional view of one of the tire-integrated wheel units that form the in-pipe moving apparatus shown in FIG. 1.
Figure 9A:
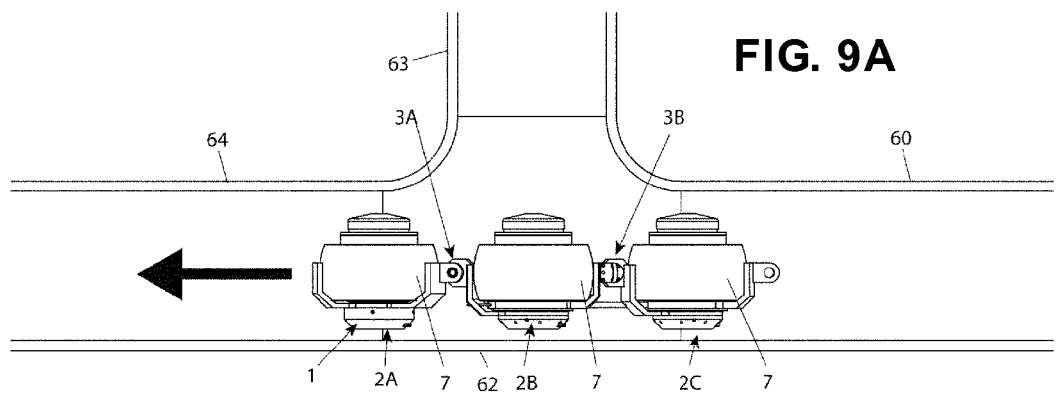
FIGS. 9A to 9C describe the action of the in-pipe moving apparatus shown in FIG. 1 that has a vertical attitude and moves straight through a T junction of a pipe, FIG. 9A being a plan view of a state immediately before the tire-integrated wheel of the third tire-integrated wheel unit enters the T junction, FIG. 9B being a plan view of a state in which the tire-integrated wheel of the third tire-integrated wheel unit has entered the T junction, and FIG. 9C being a plan view of a state in which the tire-integrated wheel of the third tire-integrated wheel unit has moved to a central portion of the T junction.
Figure 9B:
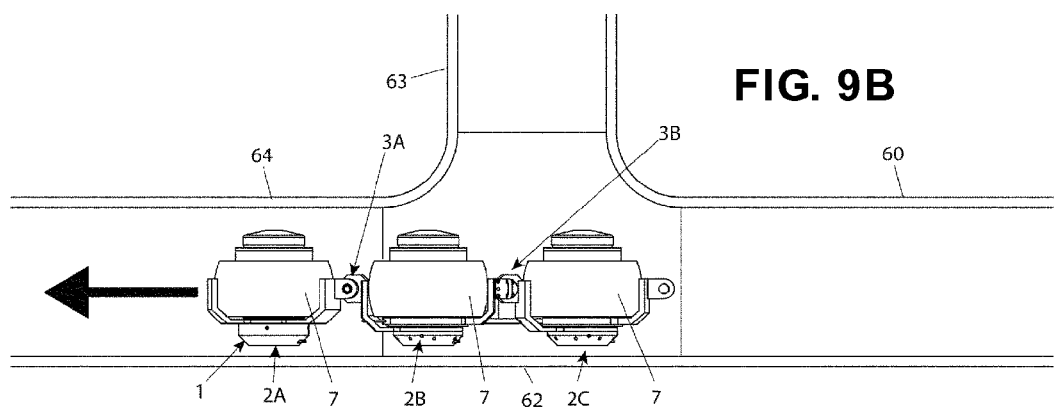
Figure 9C:
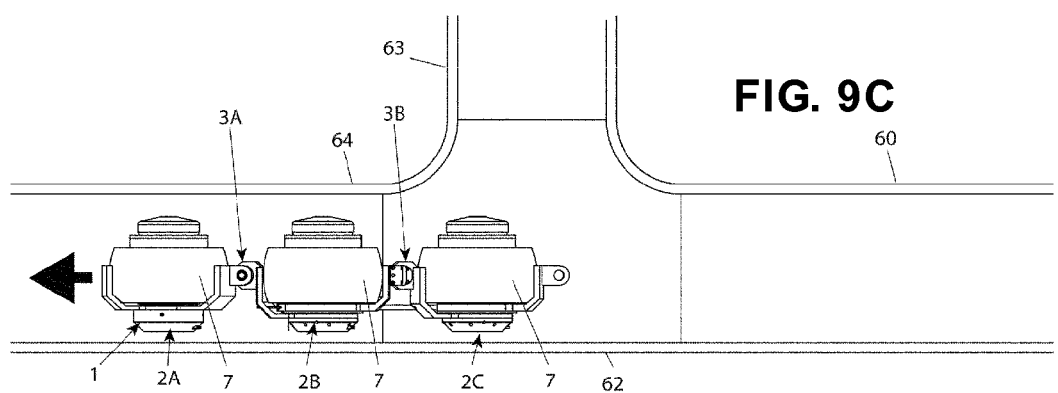
Figure 10A:
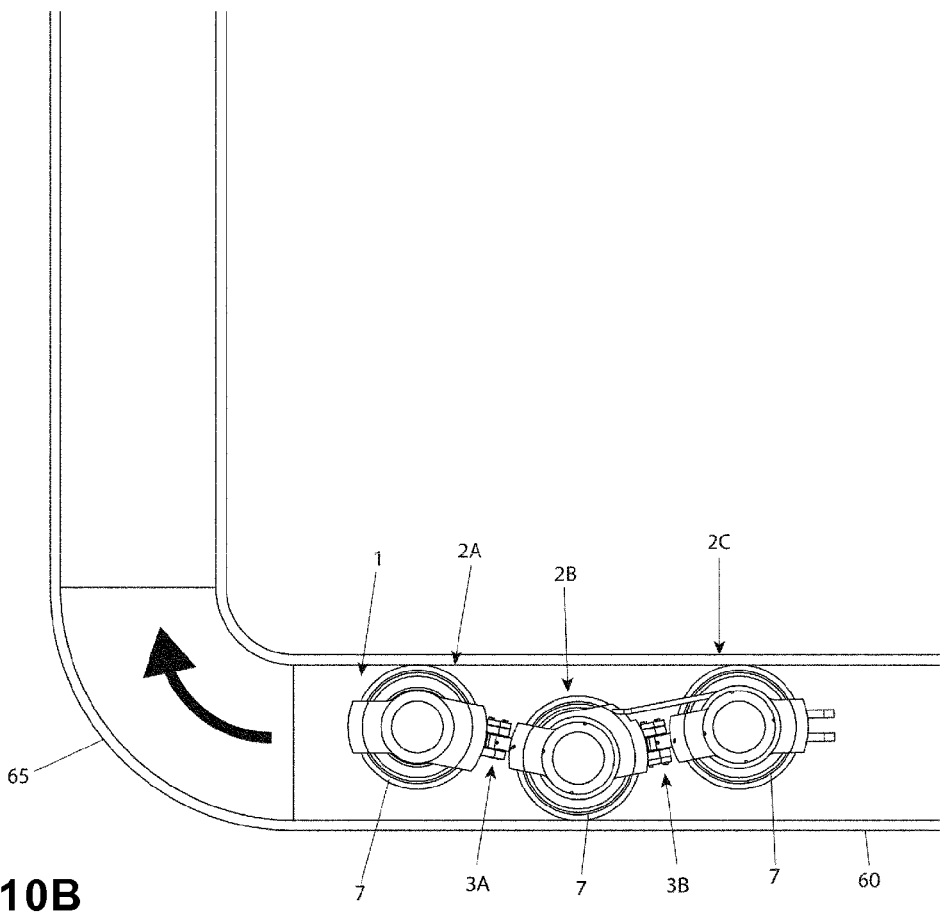
FIGS. 10A and 10B describe action of the in-pipe moving apparatus shown in FIG. 1 that has a horizontal attitude and moves through an L-shaped curve (bent segment) of a pipe, FIG. 10A being a plan view of a state in which the first tire-integrated wheel unit has moved to a point immediately before the L-shaped curve with the tire-integrated wheel in contact with the inner-side inner wall surface of the pipe and FIG. 10B being a plan view of a state immediately before the first tire-integrated wheel unit enters the L-shaped curve with the tire-integrated wheel in contact with the inner-side inner wall surface of the pipe.
Figure 10B:
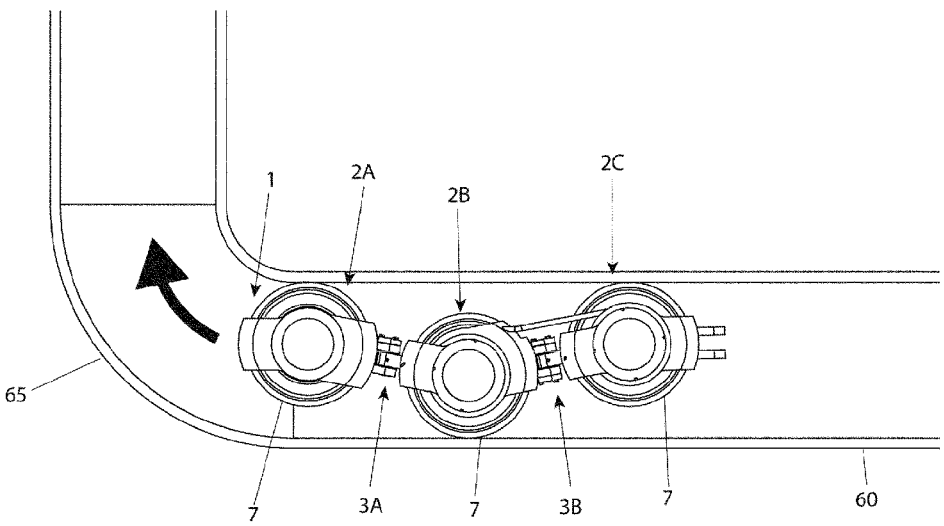

The three sets of tire-integrated wheel units 2A, 2B, and 2C have the same basic configuration except part of the components thereof and each include a drive section 10 having a motor 5, a speed reducer 6, a linkage member 8, a tubular cover body 9, and other components; a first frame 26, which is fixed to the drive section 10; a second frame 25, which is attached to the drive section 10 in a freely pivotable manner; a tire-integrated wheel 7, which is linked to a rotary shaft 11 in the drive section 10 and rotatably supported by the tubular cover body 9 via bearings 14; and other components, as shown in FIGS. 3 to 5.

The motor 5 is a prime mover that receives supplied electric power to produce mechanical power and will not be described in detail because the configuration of such a prime mover is known. The motor 5 shown in the embodiment is accommodated in a cylindrical tubular body and has a shaft protruding toward one side through a central portion of one end of the cylindrical tubular body. The shaft is linked to the rotary shaft 11 of the speed reducer 6, which has a cylindrical shape and is fixed to one side of the motor 5, and the rotary shaft 11 protrudes from a one-end-side central portion of the speed reducer 6. The speed reducer 6 reduces the number of revolutions of the motor 5 as appropriate and outputs power of the reduced number of revolutions through the rotary shaft 11, and the tubular cover body 9 is attached to the speed reducer 6 to form a unitary component. The tubular cover body 9 has a stepped section that is located on the side facing the motor 5 and forms a large-diameter section 9a, and the large-diameter section 9a provides an appropriate gap between the motor 5 and the tubular cover body 9.

Two bearings 14A and 14B are mounted around the tubular cover body 9 on axially opposite sides thereof, and the tire-integrated wheel 7 is rotatably supported via the bearings 14A and 14B and fixed to the rotary shaft 11 via the linkage member 8, whereby the motor 5 can drive and rotate the tire-integrated wheel 7. The tire-integrated wheel 7 is formed of a wheel 15, which is made of a metal and has a ring-like shape, and a tire 16, which is made of a rubber and integrated with the outer circumferential surface of the wheel 15. The bearing 14A, which is fit onto the tubular cover body 9 on the side facing the motor 5, has an outer ring fit into a hole of the wheel 15 on one axial side thereof, and the bearing 14B, which is fit onto the tubular cover body 9 on the side facing the rotary shaft 11, has an outer ring fit into the same hole of the wheel 15 on the other axial side thereof.

A bearing presser 17 is fixed to the speed reducer 6 on the side facing the linkage member 8 with fixing screws 18, and the bearing presser 17 prevents the inner ring of the bearing 17B from moving. The linkage member 8, which integrally links the rotary shaft 11 to the wheel 15, is fixed to a front end portion of the rotary shaft 11 with a locking screw 19. The linkage member 8 is formed of a disk-shaped member having a through hole provided in a central portion thereof, and a flange 8a provided around the outer circumferential edge of the linkage member 8 is provided with a plurality of insertion holes through which fixing screws 22 are inserted. The plurality of fixing screws 22, which are inserted into the insertion holes, fix the flange 8a of the linkage member 8 to a ring-shape end surface of the wheel 15.

A ring-shaped seal member 23 and a bearing 24 are fit onto the large-diameter section 9a of the tubular cover body 9. The seal member 23 is slidably in contact with the inner surface of the wheel 15 and prevents leakage of a lubricant and other substances from a space provided inside the wheel 15 and entry of water, dust, and other foreign substances from the outside. The bearing 24 is disposed in a position axially outside the seal member 23 with a predetermined gap therebetween, and the second frame 25 is pivotably attached to the drive section 10 via the bearing 24.

Figure 1:
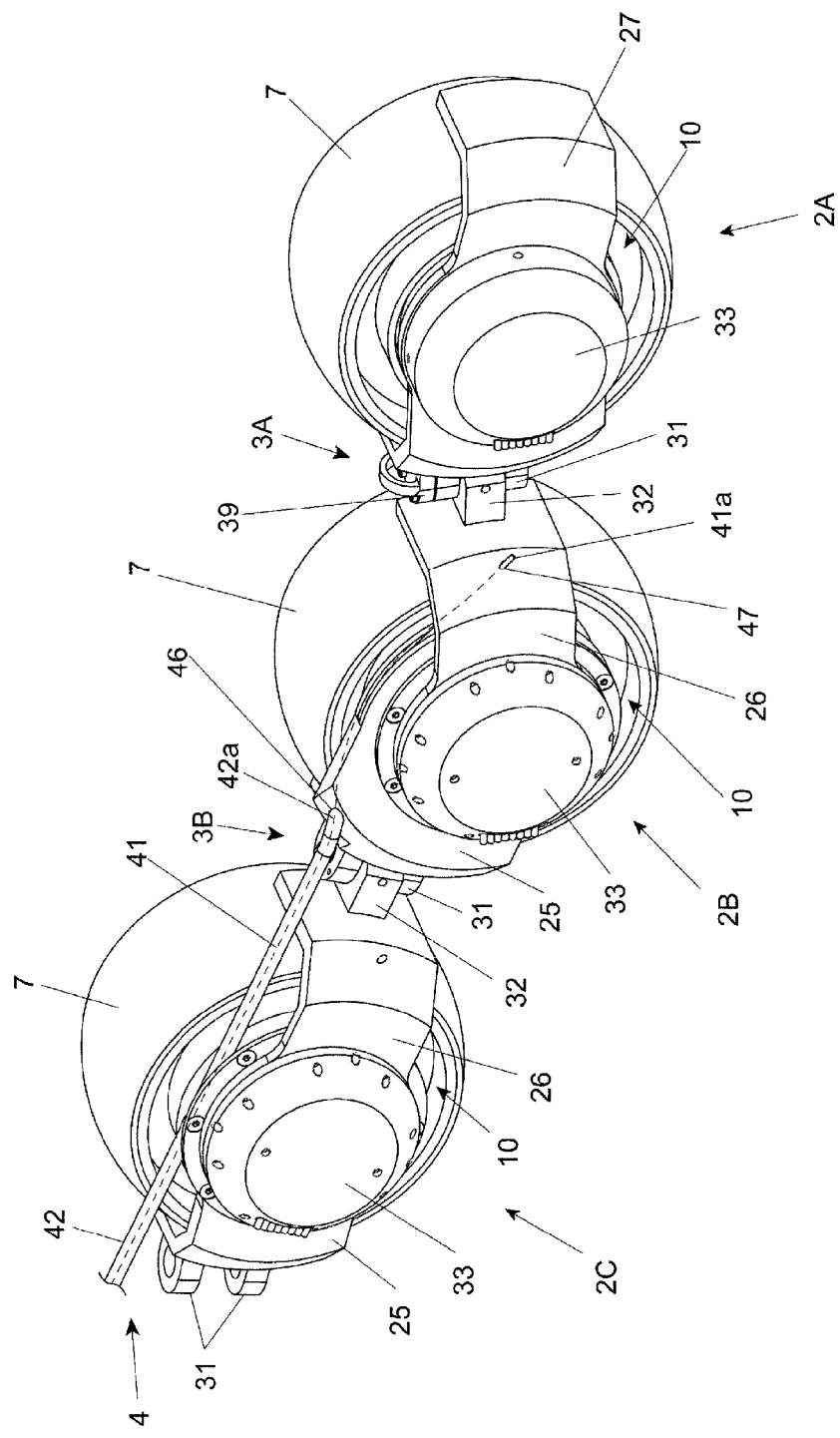
FIG. 1 is an exterior appearance perspective view showing a first embodiment of an in-pipe moving apparatus according to the invention.

The joint sections 3A and 3B have different configurations in accordance with the arrangement of the three sets of tire-integrated wheel units 2A, 2B, and 2C are disposed. That is, the first joint section 3A is formed of the following two parts: a fixed frame 27, which has the second frame 25 provided in the tire-integrated wheel unit 2A, which is the tire-integrated wheel unit of the three sets of tire-integrated wheel units 2A, 2B, and 2C, which is the first (front) tire-integrated wheel unit in the traveling direction, and the first frame 26, which is provided in the tire-integrated wheel unit 2B, which is the second tire-integrated wheel unit in the traveling direction; and the first frame 26 provided in the second tire-integrated wheel unit 2B, and the first joint section 3A pivotably links the first tire-integrated wheel unit 2A and the second tire-integrated wheel unit 2B to each other, as shown in FIGS. 1 and 3 and other figures. The second joint section 3B is formed of the following two parts: the second frame 25, which is provided in the tire-integrated wheel unit 2B, which is the second tire-integrated wheel unit in the traveling direction; and the first frame 26, which is provided in the tire-integrated wheel unit 2C, which is the third tire-integrated wheel unit in the traveling direction, and the second joint section 3B pivotably links the second tire-integrated wheel unit 2B and the third tire-integrated wheel unit 2C to each other.

Each of the second frames 25 is formed of an annular section 25a, which has a ring-like shape and into which the outer ring of the bearing 24 is fit, and an overhanging section 25b, which is so formed as to protrude outward in the radial direction from one side of the annular section 25a. A bearing stopper 28 for preventing the bearing 24 from coming out is fixed to the annular section 25a with locking screws 29. A pair of joint pieces 31, 31 are provided on the outer surface of the overhanging section 25b integrally therewith and face each other with a predetermined gap therebetween. The overhanging section 25b is so formed as to bend in a direction roughly perpendicular to the annular section 25a.

Each of the first frames 26 is formed of an annular section 26, which has a ring-like shape, and an overhanging section 26b, which is so formed as to protrude outward in the radial direction from one side of the annular section 26a. The overhanging section 26b is so formed as to bend in a direction roughly perpendicular to the annular section 26a. A joint piece 32, which is allowed to fit into the gap between the pair of joint pieces 31, 31, is provided on the outer surface of the overhanging section 26b integrally therewith. A cap 33, which covers the exterior of the motor 5, is fixed to the annular section 26a of the first frame 26 integrally therewith with a plurality of fixing screws 34.

The first frame 26 and the second frame 25 described above are both used only in the second tire-integrated wheel unit 2B and the third tire-integrated wheel unit 2C, whereas only the second frame 25 is used in the first tire-integrated wheel unit 2A and the fixed frame 27, which has that second frame 25, is attached to the first tire-integrated wheel unit 2A because no tire-integrated wheel unit is attached therebeyond. The third tire-integrated wheel unit 2C is linked to a device pulled by the in-pipe moving apparatus 1, and the device is thus pulled and moved.

The cap 33, which covers the exterior of the motor 5, includes an end surface section 33a, which has a circular shape slightly larger than the motor 5, a cylindrical section 33b, which is provided integrally and continuously with the outer circumferential edge of the end surface section 33a, and a flange section 33c, which is provided on the outer circumferential surface of the cylindrical section 32b so as to bend outward in the radial direction. A female threaded portion is provided in the inner circumferential surface of an opening-side end section of the cylindrical section 33b of the cap 33, and a male threaded portion that engages with the female threaded portion is provided in the outer circumferential surface of an opening-side end section of the large-diameter section 9a of the tubular cover body 9. The female threaded portion of the cylindrical section 33b is caused to engage with the male threaded portion of the large-diameter section 9a, whereby the cap 33 is fixed to the tubular cover body 9 integrally therewith via the threaded portions. The first frame 26 of each of the tire-integrated wheel units 2A, 2B, and 2C is fixed to the corresponding cap 33 with screws.

Specifically, in each of the two tire-integrated wheel units 2B and 2C, the cylindrical section 33b of the cap 33 is fit into the hole of the annular section 26a of the first frame 26, and in the tire-integrated wheel unit 2A, the cylindrical section 33b of the cap 33 is fit into the hole of an annular section 27a of the fixed frame 27. The second frames 25 are linked and fixed to the caps 33 with a plurality of fixing screws 34 by using a plurality of insertion holes provided in the annular sections 26a and 27a and threaded holes provided in the flange sections 33c of the caps 33.

As described above, in each of the three sets of tire-integrated wheel units 2A to 2C, the tire-integrated wheel 7 is supported in a freely rotatable manner by the tubular cover body 9 in the drive section 10 via the two bearings 14A and 14B. Further, the tire-integrated wheel 7 is integrated with the rotary shaft 11 in the drive section 10 via the linkage member 8. The second frame 25 is supported in a freely rotatable manner by the tubular cover body 9 via the bearing 24. On the other hand, the first frame 26 is coupled with the tubular cover body 9 via the cap 33, which is integrated with the first frame 26, specifically, via the threaded portions. As a result, the first frame 26 is allowed to pivot integrally with the main body of the motor 5 and the speed reducer 6, and the second frame 25 is allowed to pivot relative to the first frame 26.

The first tire-integrated wheel unit 2A and the second tire-integrated wheel unit 2B are linked to each other by the first joint section 3A swingably in a direction roughly perpendicular to the traveling direction of the tire-integrated wheels 7, so are the second tire-integrated wheel unit 2B and the third tire-integrated wheel unit 2C by the second joint section 3B. That is, the adjacent tire-integrated wheel units 2A and 2B and the adjacent tire-integrated wheel units 2B and 2C are configured to be swingable in a direction roughly perpendicular to the traveling direction of the tire-integrated wheels 7 in the tire-integrated wheel units 2A, 2B, and 2C.

The first joint section 3A is formed of the pair of joint pieces 31, 31, which are provided on the second frame 25 in the first tire-integrated wheel unit 2A, the joint piece 32, which is provided on the first frame 26 in the second tire-integrated wheel unit 2B, a pivotal shaft 35, which pivotably links the joint pieces 31 and 32 to each other, and two bearing bushes 36, 36, which support the opposite ends of the pivotal shaft 35. That is, the joint piece 32 is interposed between the pair of joint pieces 31, 31, and the single pivotal shaft 35 is inserted into holes provided through the joint pieces 31 and 32. The opposite ends of the pivotal shaft 35 are fixed to the joint pieces 31 via the bearing bushes 36.

The second joint section 3B is formed of the pair of joint pieces 31, 31, which are provided on the second frame 25 in the second tire-integrated wheel unit 2B, the joint piece 32, which is provided on the first frame 26 in the third tire-integrated wheel unit 2C, another pivotal shaft 35, which pivotably links the joint pieces 31 and 32 to each other, and another set of two bearing bushes 36, 36, which support the opposite ends of the pivotal shaft 35. That is, the joint piece 32 is interposed between the pair of joint pieces 31, 31, and the single pivotal shaft 35 is inserted into holes provided through the joint pieces 31 and 32. The opposite ends of the pivotal shaft 35 are fixed to the joint pieces 31 via the bearing bushes 36.

The axial center line of the pivotal shaft 35 is so set as to be roughly perpendicular to the axial center line of the rotary shaft 11, which is the axial center line of the tire-integrated wheel 7, in each of the drive sections 10. The phrase "roughly perpendicular" means that the inclination angle between the axial center lines is allowed to deviate from 90 degrees to some degree, but the axial center lines are optimally intersect each other exactly at 90 degrees.

When the in-pipe moving apparatus 1 passes through an L-shaped curve (bent segment) of a pipe in an attitude in which the axial center lines of the tire-integrated wheels 7 are perpendicular to the plane formed by the L-shaped curve, the in-pipe moving apparatus 1 can pass through the L-shaped curve in that attitude. When the axial center lines of the tire-integrated wheels 7 are not perpendicular to the plane described above, however, it is necessary to cause the in-pipe moving apparatus 1 to pivot around the axial center line of the pipe in such a way that the axial center lines of the tire-integrated wheels 7 are perpendicular to the plane described above. In this case, an attitude of the in-pipe moving apparatus 1 that makes it most difficult for the in-pipe moving apparatus 1 to pass through the L-shaped curve is an attitude in which the axial center lines of the tire-integrated wheels 7 are parallel to the plane described above and inclined thereto by 90 degrees. However, since each of the pivotal shafts 35 is present between the adjacent tire-integrated wheels 7, and the pivotal shaft 35 intersects the axes of the tire-integrated wheels at 90 degrees, as described above, which is the most desirable intersecting angle, the in-pipe moving apparatus 1 even in the most difficult passage attitude can be bent around the pivotal shafts 35 and can then readily pass through the L-shaped curve.

It is, however, noted that the intersecting angle between the axial center line of the rotary shaft 11 and the pivotal shaft 35 can be set at any value greater than or equal to 45 degrees but smaller than or equal to 135 degrees. The reason for this is that in an attempt to cause the in-pipe moving apparatus 1 to pass through an L-shaped curve in an arbitrary attitude, the intersecting angle that varies over the range greater than or equal to 45 degrees but smaller than or equal to 135 degrees allows the overall attitude of the in-pipe moving apparatus 1 to be deformed in accordance with the L-shaped curve and allows the in-pipe moving apparatus 1 to pass therethrough.

The fixed frame 27 in the first joint section 3A is provided with a potentiometer 38 for detecting swing angles of the first tire-integrated wheel unit 2A and the second tire-integrated wheel unit 2B in the upward/downward direction and the rightward/leftward direction. A meter cover 39 is attached to the potentiometer 38 and protects the potentiometer 38.

One side of the bending generator 4 is fixed to the second tire-integrated wheel unit 2B, as shown in FIGS. 1 and 4 and other figures. The bending generator 4 imparts tensile force to the three sets of tire-integrated wheel units 2A to 2C so as to bend them in the direction perpendicular to a floor or any other surface and achieve a V-shaped attitude. In this embodiment, the bending generator 4 is formed of a cable 41, a tube 42, a case 43, a coil spring 44, and a traction force adjustment unit 45, which fixes the coil spring 44 to the case 43, as shown in FIG. 6A. The traction force adjustment unit 45 not only adjusts the spring force in accordance with the state of a pipe but also nullifies the spring force of the coil spring 44 to allow the in-pipe moving apparatus 1 to be extracted out of the pipe in case of an emergency. The case 43 is formed of a tubular member having a cylindrical space, and the coil spring 44 in an extended state is accommodated in the space in the case 43. One end of the tube 42 is fixed to one axial side of the case 43.

The traction force adjustment unit 45, which fixes the coil spring 44 to the case 43, is a device for not only adjusting the pressure applied by the in-pipe moving apparatus 1 to the interior of a pipe to produce propulsion force necessary for movement of the apparatus to achieve appropriate pressure for prevention of an increase in propulsion resistance but also nullifying the pressing force from the tire-integrated wheels 7 against the inner wall of the pipe when the in-pipe moving apparatus 1 malfunctions in the pipe to allow the in-pipe moving apparatus 1 to be readily extracted out of the pipe.

A front end 42a of the tube 42 is fit into a through hole 46 provided in the second frame 25 in the second tire-integrated wheel unit 2B so as to be fixed. One end of the coil spring 44 is fixed to the case 43, and one end of the cable 41 is linked to the other end of the coil spring 44. The cable 41 passes through the tube 42, and the protruding side of the cable 41 passes through the through hole in the second frame 25, passes through the second frame 25, and reaches the first frame 26. The front end 41a of the cable 41 is inserted into an insertion hole 47 provided in the first frame 26 and fixed there.

Figure 2A:
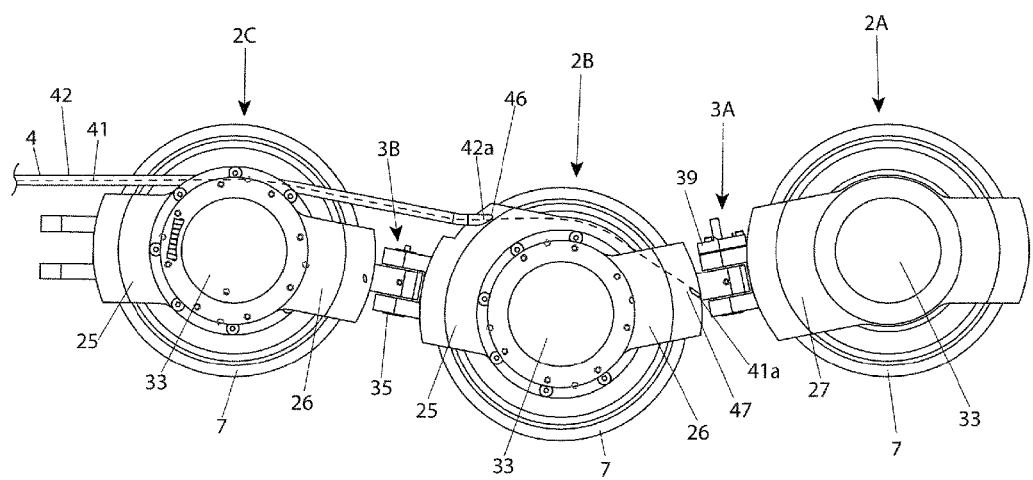
FIGS. 2A and 2B show the first embodiment of the in-pipe moving apparatus according to the invention, FIG. 2A being a side view and FIG. 2B being a plan view.
Figure 2B:
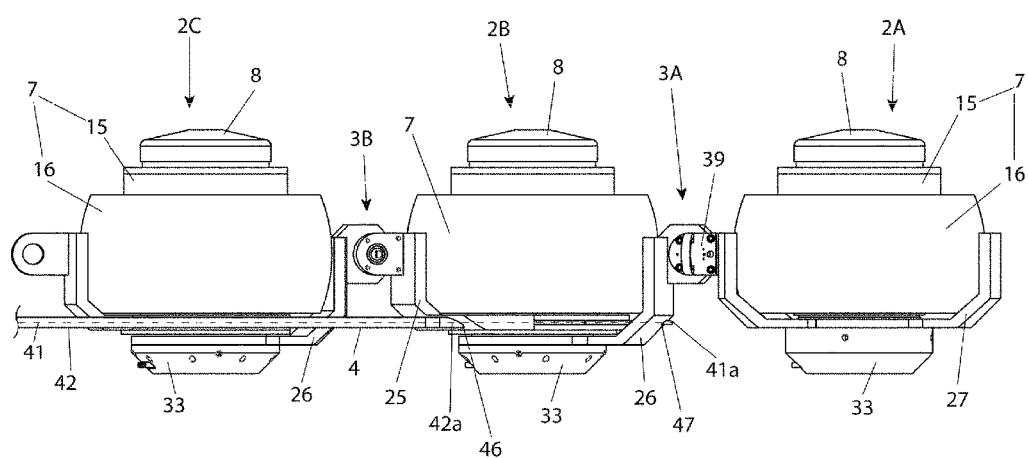

To fix the front end 41a of the cable 41 to the first frame 26, the coil spring 44 is pulled as appropriate to achieve a state in which tensile force keeps acting on the first frame 26. The spring force produced by the coil spring 44 imparts a rotational force that causes the first frame 26 to rotate toward the cable 41 with respect to the second frame 25 in the second tire-integrated wheel unit 2B. As a result, the attitude of the three sets of tire-integrated wheel units 2A, 2B, and 2C is so controlled that the first tire-integrated wheel unit 2A and the third tire-integrated wheel unit 2C are urged around the second tire-integrated wheel unit 2B so as to approach each other on the side where the cable 41 is present, whereby the apparatus is bent in a V-like shape in the direction perpendicular to surfaces with which the tire-integrated wheels 7 come into contact, as shown in FIG. 2A.

FIGS. 6A and 6B describe a state in which a vision device 50, a control device 51, an inspection device 52, and a controller 53 are connected to the in-pipe moving apparatus 1 having the configuration described above and the in-pipe moving apparatus 1 with the devices is caused to move through a pipe 60. The vision device 50 visually recognizes the state of the interior of the pipe 60 and can, for example, be formed of a monitoring camera. The control device 51 controls the action of the three sets of tire-integrated wheel units 2A to 2C and includes, for example, a microcomputer and other necessary electronic parts, a wiring substrate on which the electronic parts are mounted and which is provided with a necessary electronic circuit, and a housing that accommodates the components described above.

The inspection device 52 is an object to be transported by the in-pipe moving apparatus 1 and a device that inspects the inner diameter, thickness, and other parameters of the pipe 60 and determines whether or not cracking, corrosion, and other types of defects of the pipe have occurred. The inspection device 52 can, for example, be an ultrasonic sensor or an eddy current flaw detection sensor. The controller 53 controls and drives the control device 51 and the inspection device 52 on the basis of information from the vision device 50 and is manually operated by an operator outside the pipe 60. The bending generator 4 is configured to adjust the tensile force at a predetermined value as an initial setting in the present embodiment. It is, however, noted that the tension controlled by the bending generator can, of course, be adjusted to be greater or smaller than the predetermined value, as will be described later.

Traveling action of the in-pipe moving apparatus 1 will next be described.

FIG. 7 to FIGS. 9A to 9C describe action of the in-pipe moving apparatus 1 in which the in-pipe moving apparatus 1 moves straight through a T junction 62, which is a horizontally branched segment of the pipe 60, in an attitude in which the shafts of the tire-integrated wheels are maintained horizontal and show a case where a bifurcating passage 63 extends in the horizontal direction. In this case, the spring force produced by the coil spring 44 in the tension imparting member 4 causes, among the tire-integrated wheels 7 of the three sets of tire-integrated wheel units 2A to 2C, the tire-integrated wheels 7, 7 in the first and third tire-integrated wheel units to be pressed against the lower inner surface (far-side surface) {or upper surface (near-side surface)} of the pipe 60 and the tire-integrated wheel 7 in the second tire-integrated wheel unit to be pressed against the opposite surface of the pipe 60, that is, the upper inner surface (near-side surface) {or lower surface (far-side surface)} of the pipe 60. In this state, the operator operates the controller 53 to drive the motors 5 in the three sets of tire-integrated wheel units 2A to 2C at the same speed under the control of the control device 51. As a result, the in-pipe moving apparatus 1 can move straight through a linear passage 64 with the longitudinal cross-section of each of the tire-integrated wheels 7 maintained vertical. FIGS. 8A, 8B, 8C and FIGS. 9A, 9B, and 9C show intermediate states of the movement.

FIGS. 10A and 10B to FIGS. 12A and 12B describe action of the in-pipe moving apparatus 1 in which the in-pipe moving apparatus 1 moves through an L-shaped bent segment (L-shaped curve) 65, which is a vertically bent segment of the pipe 60, in an attitude in which the shafts of the tire-integrated wheels 7 are maintained horizontal. The same description applied to a case where the bent segment 65 is a horizontally bent segment. In the present embodiment, the spring force produced by the coil spring 44 in the tension imparting member 4 causes, among the tire-integrated wheels 7 of the three sets of tire-integrated wheel units 2A to 2C, the tire-integrated wheels 7, 7 of the first and third tire-integrated wheel units to be pressed against the inner-side surface that is an inner surface of the bent segment 65 and has a smaller radius of curvature and the tire-integrated wheel 7 of the second tire-integrated wheel unit to be pressed against the opposite outer-side surface that is an inner surface of the bent segment 65 and has a larger radius of curvature.

In this state, the operator controls the controller 53 to drive the motors 5 in the three sets of tire-integrated wheel units 2A to 2C at the same speed under the control of the control device 51. As a result, the in-pipe moving apparatus 1 can pass through the bent segment 65 with the axes of rotation of the tire-integrated wheels 7 maintained horizontal. FIGS. 10A, 10B, 11A, 11B, 11C, 12A, and 12B show intermediate states of the movement. In this case, the tire-integrated wheels 7, 7 of the first and third tire-integrated wheel units keep pressed against the inner-side inner surface of the bent segment 65, and the tire-integrated wheel 7 of the second tire-integrated wheel unit keeps pressed against the outer-side inner surface of the bent segment 65.

Figure 13A:
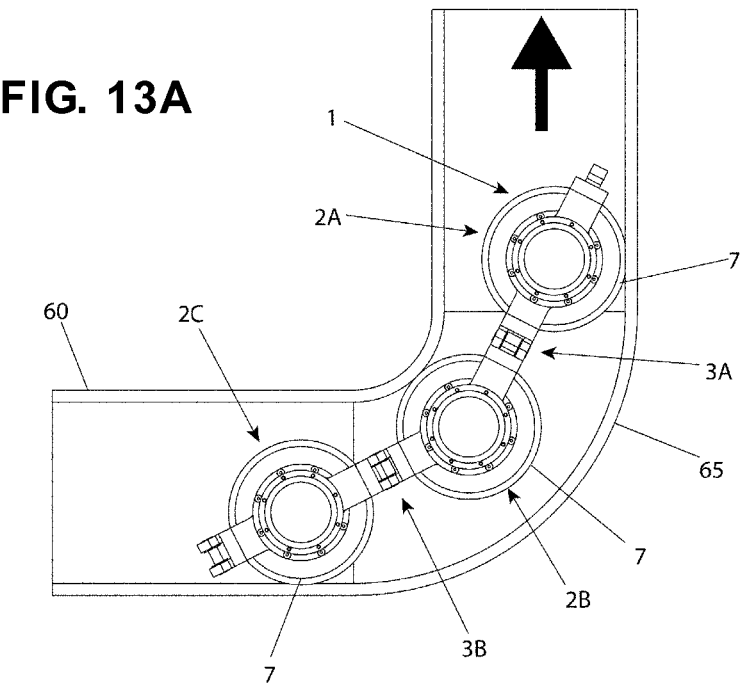
FIGS. 13A and 13B describe action of the in-pipe moving apparatus shown in FIG. 1 that has the horizontal attitude and passes through an L-shaped curve of a pipe, FIG. 13A being a plan view of a state in which the in-pipe moving apparatus passes through the L-shaped curve with the tire-integrated wheels of the first and third tire-integrated wheel units in contact with the outer-side inner wall surface of the pipe and the tire-integrated wheel of the second tire-integrated wheel unit in contact with the inner-side inner wall surface of the pipe, and FIG. 13B being a perspective view of the same state.
Figure 13B:
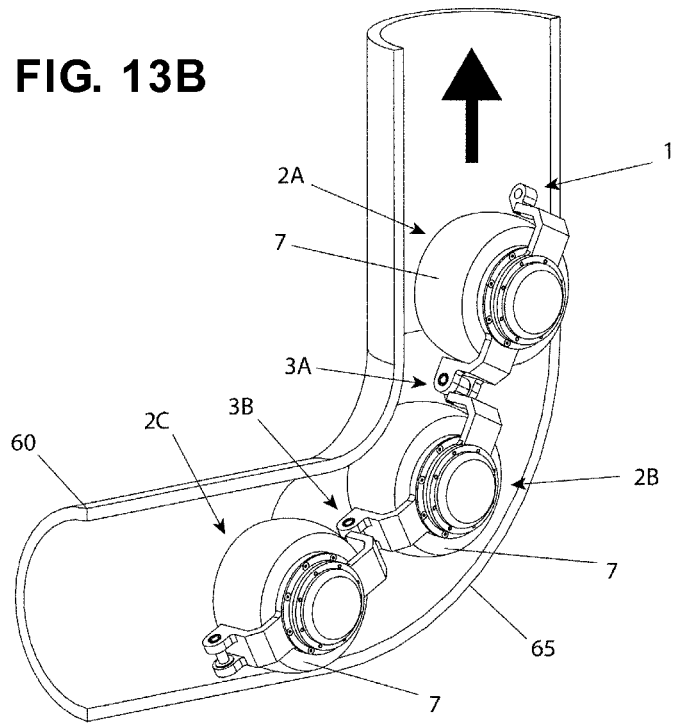

FIGS. 13A and 13B describe action of the in-pipe moving apparatus 1 in which the in-pipe moving apparatus 1 in the horizontal attitude moves through an L-shaped bent segment 65 of a pipe 60, which is a horizontally bent segment, and the present example differs the example shown in FIGS. 10A and 10B to 12A and 12B in that among the tire-integrated wheels 7 of the three sets of tire-integrated wheel units 2A, 2B, and 2C, the tire-integrated wheel 7 of the first tire-integrated wheel unit 2A and the tire-integrated wheel 7 of the third tire-integrated wheel unit 2C are pressed against the outer-side surface of the bent segment 65 that is an inner surface of the bent segment 65 and has a large radius of curvature and the tire-integrated wheel 7 of the second tire-integrated wheel unit 2B is pressed against the opposite inner-side surface of the bent segment 65 that is an inner surface of the bent segment 65 and has a small radius of curvature. The other types of action are the same as those in the example described above.

FIGS. 14A and 14B and FIGS. 15A to 15C describe action of the in-pipe moving apparatus 1 in which the in-pipe moving apparatus 1 in the vertical attitude moves through the L-shaped bent segment 65 (L-shaped curve) of the pipe 60, which is a horizontally bent segment, and the present example differs the example shown in FIGS. 10A and 10B to 12A and 12B in that the in-pipe moving apparatus 1 has an attitude in which the tire-integrated wheels 7 of the three sets of tire-integrated wheel units 2A to 2C are perpendicular to a floor with the tire-integrated wheels 7 of the first tire-integrated wheel unit 2A and the third tire-integrated wheel unit 2C pressed against the lower inner surface (far-side inner surface) {or upper inner surface (near-side inner surface)} of the bent segment 65 and the tire-integrated wheel 7 of the second tire-integrated wheel unit 2B pressed against the upper inner surface (near-side inner surface) {or lower inner surface (far-side inner surface)} of the bent segment 65.

Figure 14A:
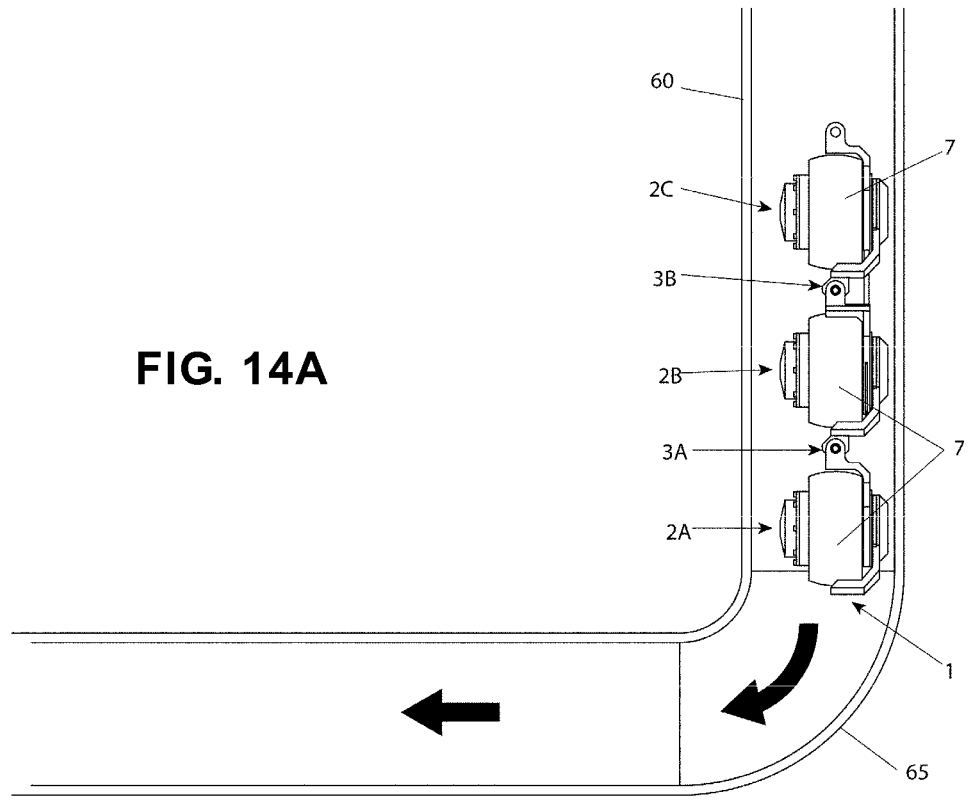
FIGS. 14A and 14B describe action of the in-pipe moving apparatus shown in FIG. 1 that has the vertical attitude and moves through an L-shaped curve (bent segment) of a pipe, FIG. 14A being a plan view of a state in which the first tire-integrated wheel unit has moved to a point immediately before the L-shaped curve with the tire-integrated wheel thereof in contact with the upper inner surface (or lower inner surface) of the pipe and FIG. 14B being a plan view of a state in which the tire-integrated wheel of the first tire-integrated wheel unit has entered the L-shaped curve.
Figure 14B:
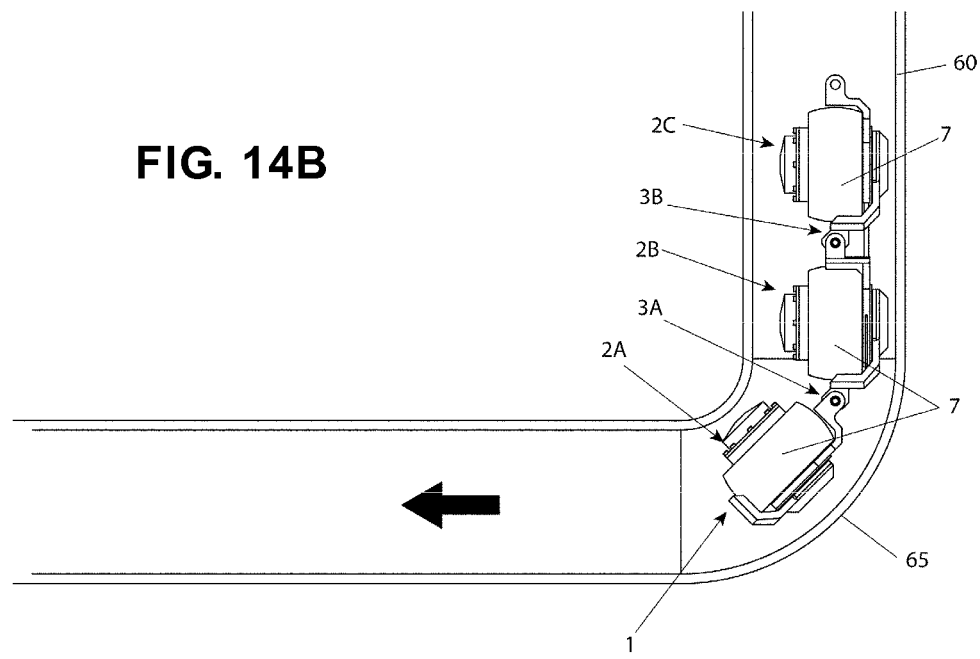
Figure 15A:
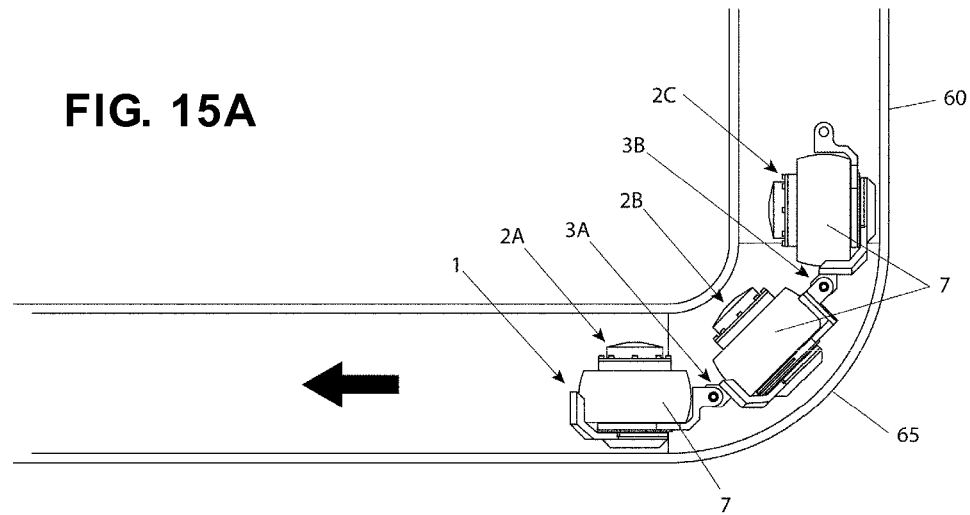
FIGS. 15A to 15C describe the action of the in-pipe moving apparatus shown in FIG. 1 that has the vertical attitude and moves through an L-shaped curve of a pipe, FIG. 15A being a plan view of a state in which the tire-integrated wheel of the second tire-integrated wheel unit has moved to the L-shaped curve, FIG. 15B being a plan view of a state in which the tire-integrated wheel of the third tire-integrated wheel unit has moved to the L-shaped curve, and FIG. 15C being a plan view of a state in which the tire-integrated wheel of the third tire-integrated wheel unit has passed through the L-shaped curve.

In the state shown in FIG. 14A, the tire-integrated wheels 7 to 7 of the three sets of tire-integrated wheel units 2A to 2C are so driven as to rotate at the same speed and enter the bent segment 65 in the attitude in which the tire-integrated wheel 7 are maintained vertical. In the bent segment 65, the tire-integrated wheel 7 of the first tire-integrated wheel unit 2A is pressed by the spring force produced by the coil spring 44 in the tension imparting member 4 against the upper inner surface of the pipe 60 that is a surface thereof located at the highest level with respect to the plane of view (or lower inner surface located at the lowest level) and guided by the passage inner wall of the upper inner surface (or lower inner surface) to arcuately move through a central portion of the bent segment 65 along the curve thereof, as shown in FIG. 14B. Similarly, the tire-integrated wheel 7 of the second tire-integrated wheel unit 2B is pressed by the spring force produced by the coil spring 44 in the tension imparting member 4 against the lower inner surface of the pipe 60 that is a surface thereof located at the lowest level (or upper inner surface located at the highest level) and guided by the lower inner surface (or upper inner surface) to arcuately move through the central portion of the curved segment 65 along the curve thereof, as shown in FIG. 15A.

Figure 15B:
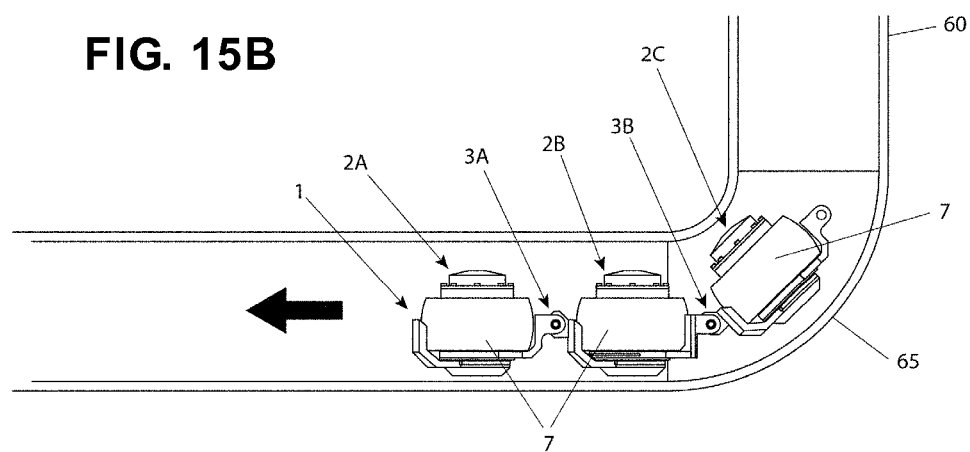
Figure 15C:
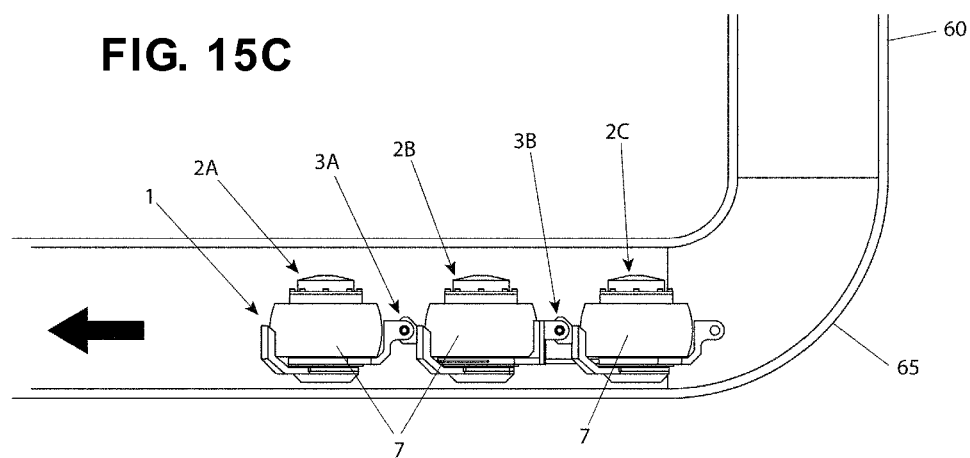
Figure 16:
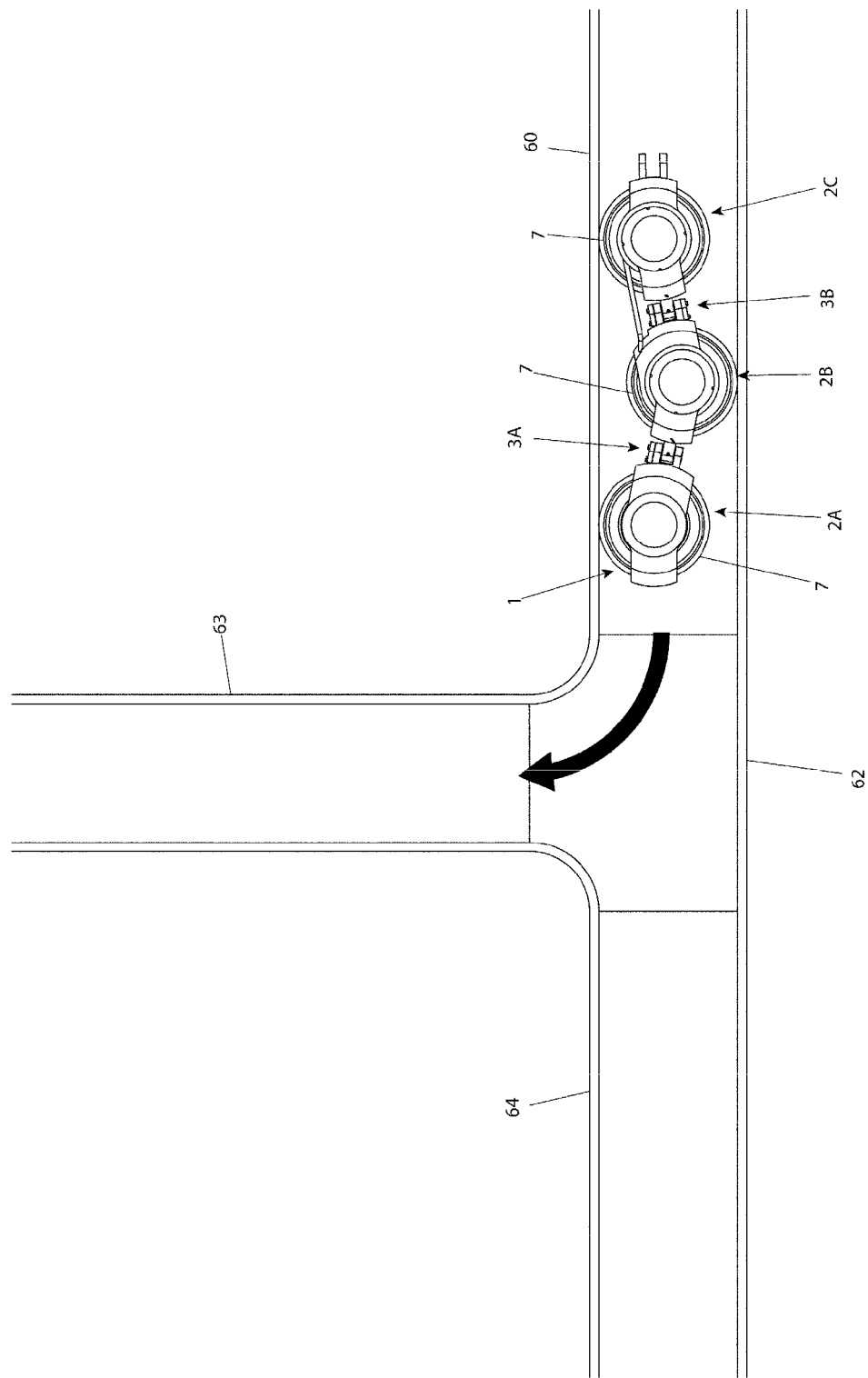
FIG. 16 describes action of the in-pipe moving apparatus shown in FIG. 1 that has the horizontal attitude and enters a bifurcating passage from a T junction of a pipe and is a plan view of a state in which the tire-integrated wheel of the first tire-integrated wheel unit has moved to a point before the bifurcating passage.
Figure 17A:
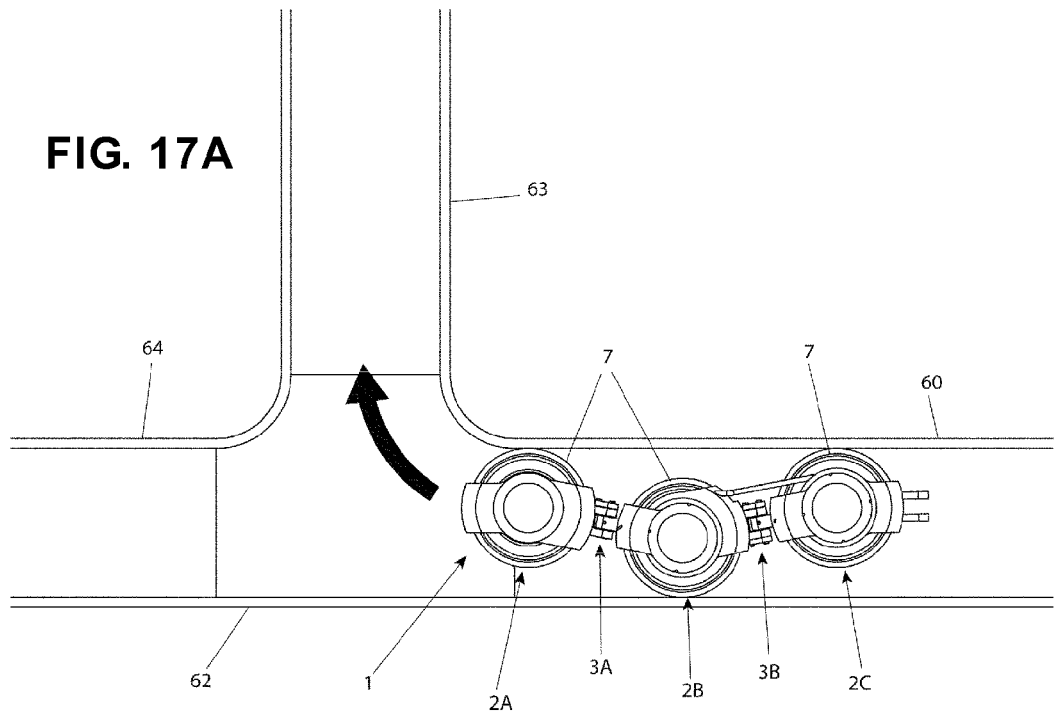
FIGS. 17A and 17B describe the action of the in-pipe moving apparatus shown in FIG. 1 having the horizontal attitude and enters a bifurcating passage from a T junction of a pipe, FIG. 17A being a plan view of a state immediately before the tire-integrated wheel of the first tire-integrated wheel unit enters the bifurcating passage and FIG. 17B being a plan view of a state in which the tire-integrated wheel of the first tire-integrated wheel unit has entered the bifurcating passage.
Figure 17B:
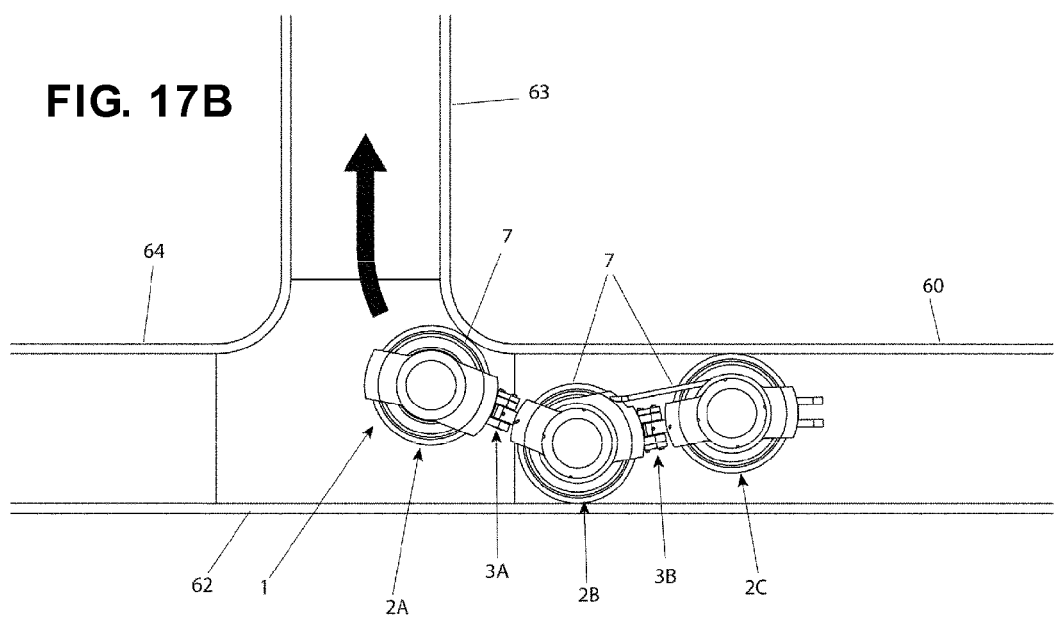
Figure 18A:
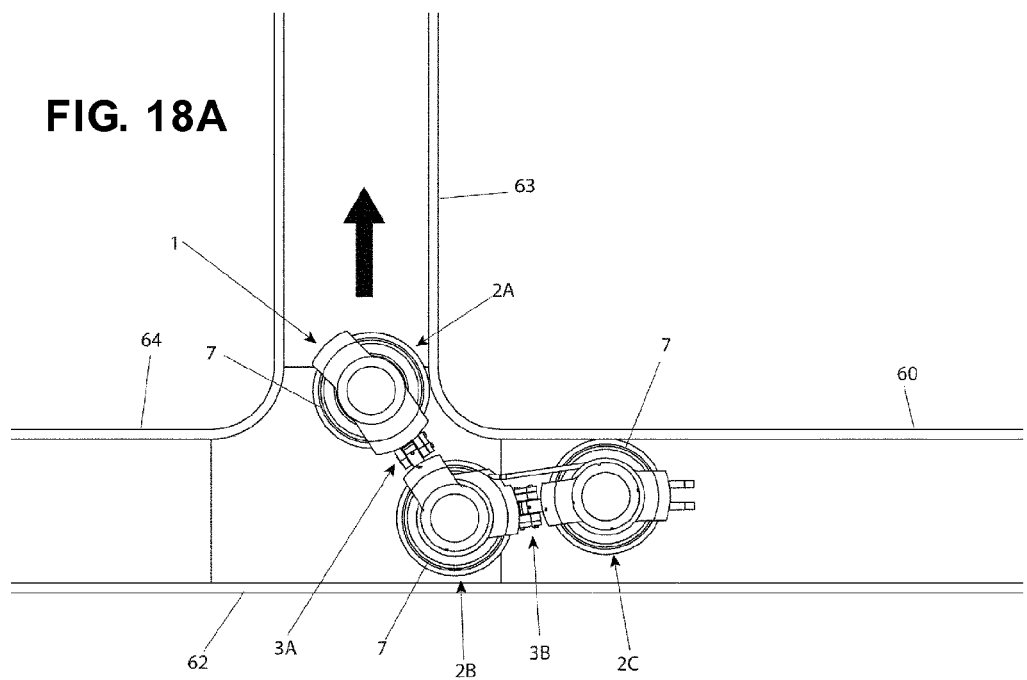
FIGS. 18A and 18B describe the action of the in-pipe moving apparatus shown in FIG. 1 that has the horizontal attitude and enters a bifurcating passage from a T junction of a pipe, FIG. 18A being a plan view of a state in which the tire-integrated wheel of the second tire-integrated wheel unit has entered the bifurcating passage and FIG. 18B being a plan view of a state immediately after the tire-integrated wheel of the third tire-integrated wheel unit has entered the bifurcating passage.
Figure 18B:
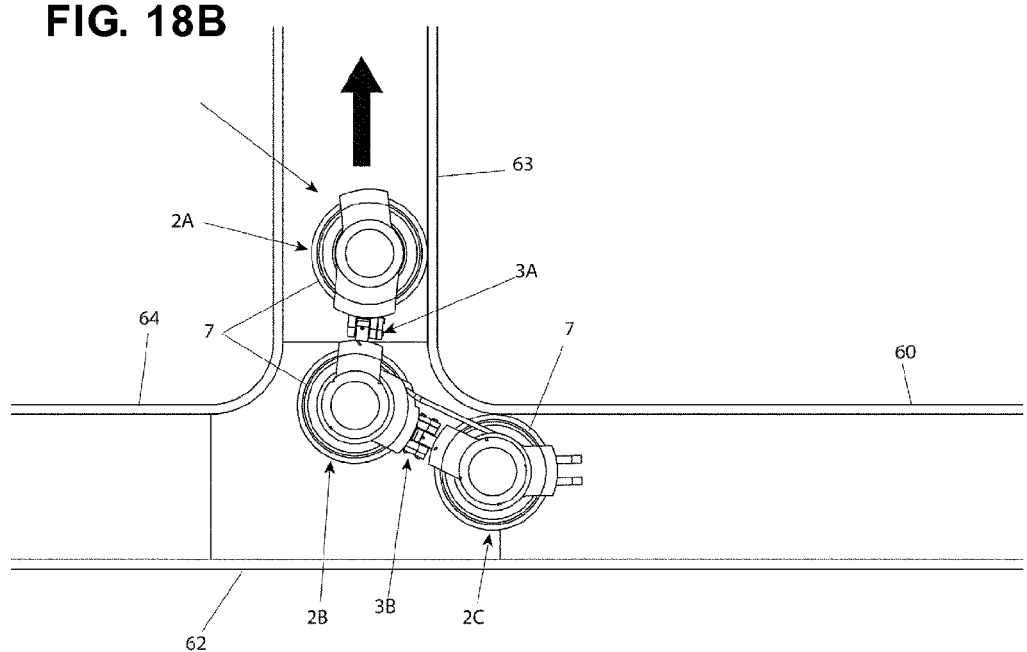
Figure 19A:
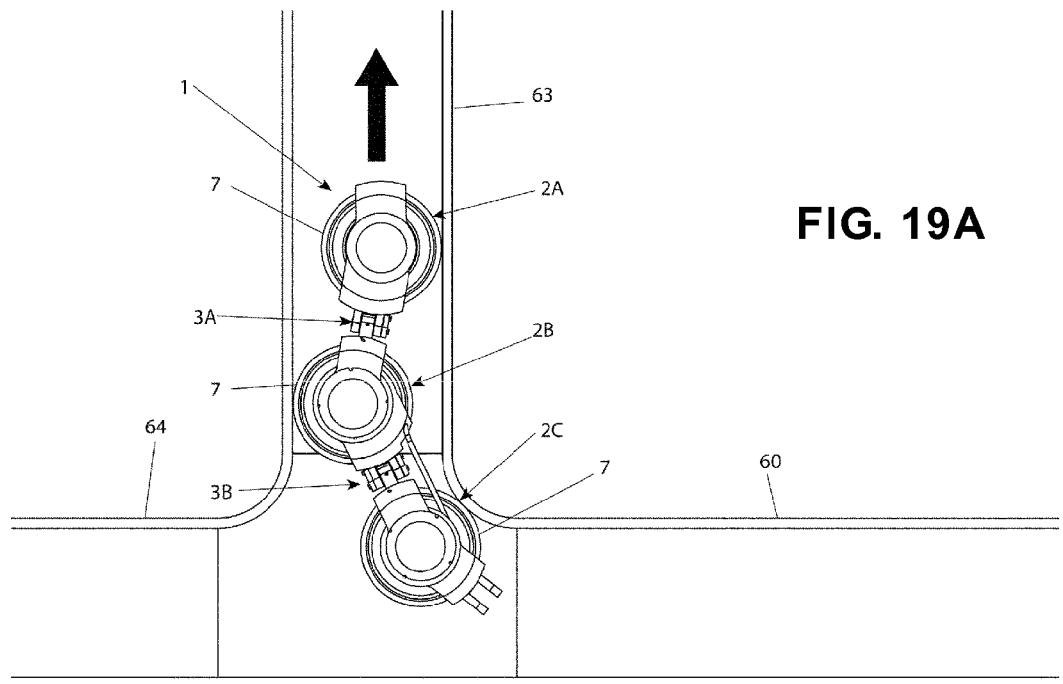
FIGS. 19A and 19B describe the action of the in-pipe moving apparatus shown in FIG. 1 that has the horizontal attitude and enters a bifurcating passage from a T junction of a pipe, FIG. 19A being a plan view of a state in which the tire-integrated wheel of the third tire-integrated wheel unit has entered the bifurcating passage and FIG. 19B being a plan view of a state immediately after the tire-integrated wheel of the third tire-integrated wheel unit has passed through the bifurcating passage.
Figure 19B:
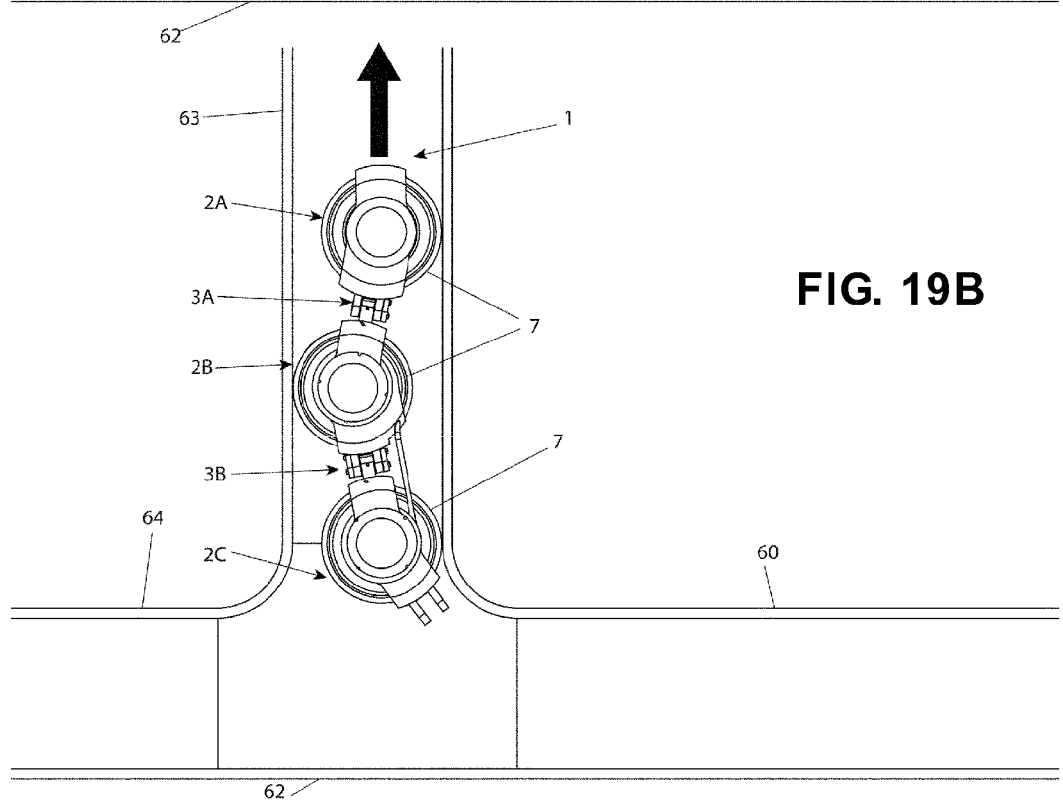

Further, the tire-integrated wheel 7 of the following third tire-integrated wheel unit 2C is pressed by the spring force produced by the coil spring 44 in the tension imparting member 4 against the upper inner surface of the pipe 60 that is a surface thereof located at the highest level with respect to the plane of view (or lower inner surface located at the lowest level) and guided by the upper inner surface (or lower inner surface) to arcuately move through the central portion of the bent segment 65 along the curve thereof, as shown in FIG. 15B. The in-pipe moving apparatus 1 can then pass through the bent segment 65 in the state in which the initial vertical attitude is maintained, as shown in FIG. 15C.

FIGS. 16 to 19A and 19B describe action of the in-pipe moving apparatus 1 in which the in-pipe moving apparatus 1 in the horizontal attitude enters the bifurcating passage 63 from the T junction 62 of the pipe 60, which is a horizontally branched segment, and the same description applies to a case where the bifurcating passage 63 extends upward in the vertical direction. In the present example, the spring force produced by the coil spring 44 in the tension imparting member 4 presses, among the tire-integrated wheels 7 of the three sets of tire-integrated wheel units 2A to 2C, the tire-integrated wheels 7, 7 of the first and third tire-integrated wheel units against the inner-side inner surface of the T junction 62 and the tire-integrated wheel of the second tire-integrated wheel unit against the outer-side inner surface of the T junction 62.

In this state, the operator operates the controller 53 to drive the motors 5 in the three sets of tire-integrated wheel units 2A to 2C at the same speed under the control of the control device 51. As a result, the in-pipe moving apparatus 1 can smoothly enter the bifurcating passage 63 and move therethrough with the tire-integrated wheel shafts, which are centers of rotation of the tire-integrated wheels 7, maintained vertical. FIGS. 16, 17A, 17B, 18A, 18B, 19A, and 19B show intermediate states of the movement. In this case, the tire-integrated wheels 7, 7 of the first and third tire-integrated wheel units keep pressed against the inner-side inner side surface of the bifurcating passage 63, and the tire-integrated wheel 7 of the second tire-integrated wheel unit keeps pressed against the outer-side inner side surface of the bifurcating passage 63.

FIGS. 20A and 20B to FIGS. 22A to 22C describe action of the in-pipe moving apparatus 1 in which the in-pipe moving apparatus 1 in the horizontal attitude enters the bifurcating passage 63 from the T junction 62, which is part of the pipe 60 and a horizontally branched segment, and the same description applies to a case where the bifurcating passage 63 extends upward in the vertical direction. The present example differs from the example shown in FIGS. 16 to 19A and 19B in that at a point a certain distance before the in-pipe moving apparatus 1 enters the bifurcating passage 63, among the tire-integrated wheels 7 to 7 of the three sets of tire-integrated wheel units 2A to 2C, the tire-integrated wheel 7 of the second tire-integrated wheel unit is pressed against the inner-side inner surface of the bifurcating passage 63 and the tire-integrated wheels 7, 7 of the first and third tire-integrated wheel units are pressed against the outer-side inner surface of the bifurcating passage 63 of the pipe 60.

In this state, in which the tire-integrated wheel 7 of the first tire-integrated wheel unit 2A is in contact with a linear segment on the side opposite the bifurcating passage 63 of the T junction 62, the in-pipe moving apparatus 1 cannot enter the bifurcating passage 63 even when the in-pipe moving apparatus 1 is caused to move straight in the same attitude because the tire-integrated wheel 7 of the first tire-integrated wheel unit is guided by the inner side surface of the linear segment. Therefore, in this case, the attitude of the in-pipe moving apparatus 1 needs to be controlled at a point a predetermined distance before the in-pipe moving apparatus 1 enters the bifurcating passage 63 in such a way that the tire-integrated wheels 7, 7 of the first and third tire-integrated wheel units are pressed against the inner-side inner side surface of the bifurcating passage 63 and the tire-integrated wheel 7 of the second tire-integrated wheel unit is pressed against the outer-side inner side surface of the bifurcating passage 63.

Figure 20A:
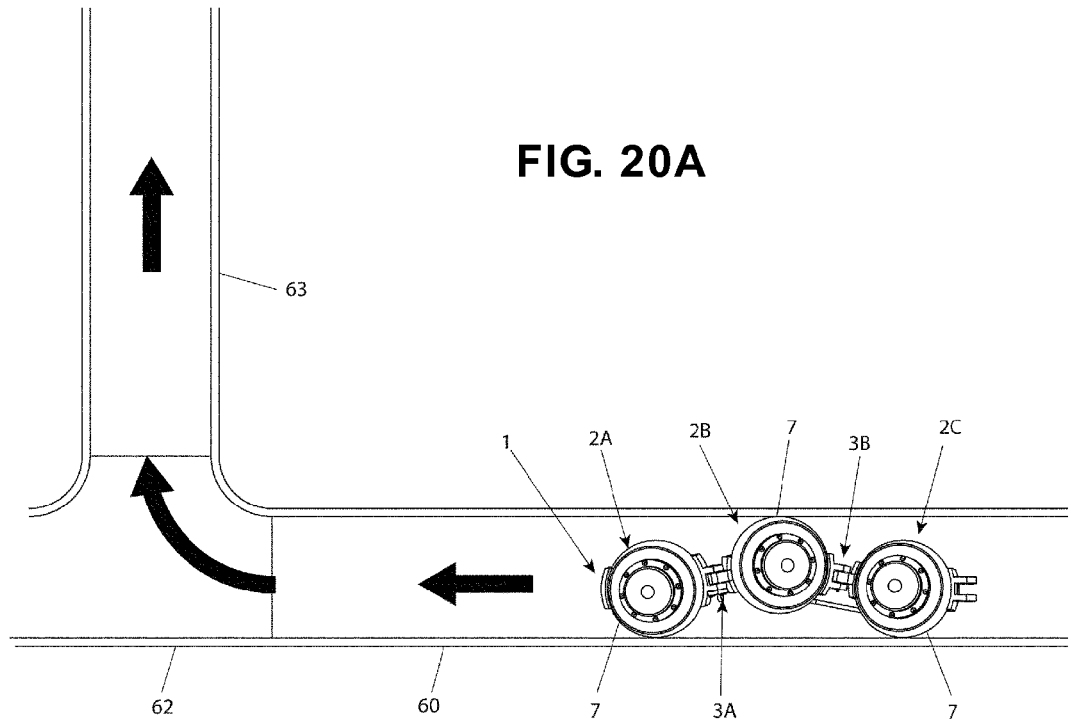
FIGS. 20A and 20B describe attitude control action of the in-pipe moving apparatus according to the first embodiment of the invention, FIG. 20A being a plan view of a state in which the tire-integrated wheels of the three sets of tire-integrated wheel units move in the horizontal attitude and FIG. 20B being a plan view of a state in which the attitude is rotated by about 30 degrees from the state in FIG. 20A.

The attitude of the in-pipe moving apparatus 1 in this case can be controlled, for example, as follows: First, at a point a predetermined distance before the in-pipe moving apparatus 1 reaches the bifurcating passage 63, the operator operates the controller 53 to set the three motors 5 to 5 in the three sets of tire-integrated wheel units 2A to 2C at different numbers of revolutions under the control of the control device 51, as shown in FIG. 20A. That is, the number of revolutions of the tire-integrated wheel 7 of the second tire-integrated wheel unit 2B (N2) is set to be greater than the number of revolutions of the tire-integrated wheel 7 of the first tire-integrated wheel unit 2A (N1); and the number of revolutions of the tire-integrated wheel 7 of the third tire-integrated wheel unit 2C (N3) is set to be greater than the number of revolutions of the tire-integrated wheel 7 of the second tire-integrated wheel unit 2B (N2) (N1<N2<N3).

Figure 20B:
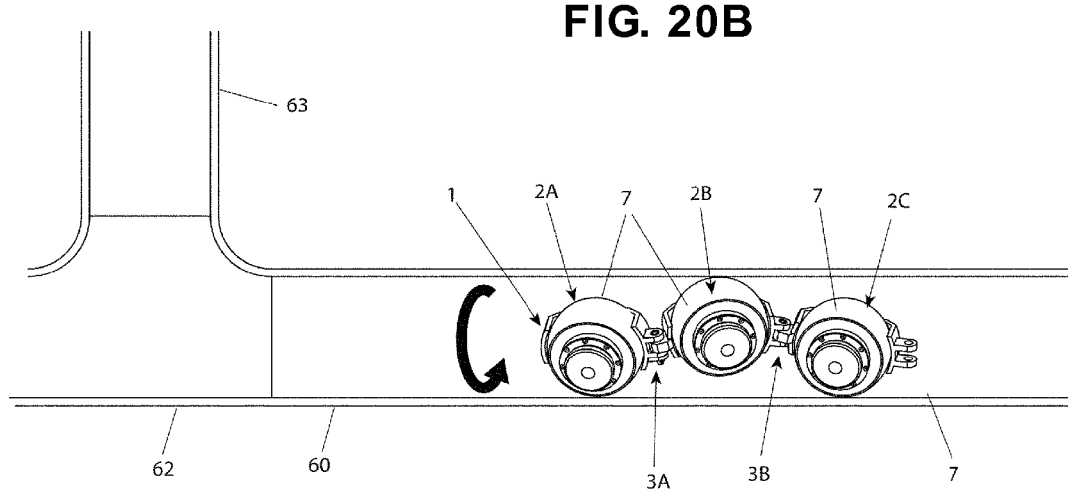

As a result, since the number of revolutions of the tire-integrated wheel 7 located behind is greater than the number of revolutions of the tire-integrated wheel 7 located ahead, a state in which the tire-integrated wheel located ahead in the traveling direction is pushed by the tire-integrated wheel located behind in the traveling direction occurs, as shown in FIG. 20A, and the state sequentially transitions to the following states: the state shown in FIG. 20B (state in which the in-pipe moving apparatus 1 is rotated by about 30 degrees from the state shown in FIG. 20A); the state shown in FIG. 21A (state in which the in-pipe moving apparatus 1 is rotated by about 60 degrees from the state shown in FIG. 20A); the state shown in FIG. 21B (state in which the in-pipe moving apparatus 1 is rotated by about 90 degrees from the state shown in FIG. 20A); the state shown in FIG. 21C (state in which the in-pipe moving apparatus 1 is rotated by about 120 degrees from the state shown in FIG. 20A); the state shown in FIG. 22A (state in which the in-pipe moving apparatus 1 is rotated by about 150 degrees from the state shown in FIG. 20A); and the state shown in FIG. 22B (state in which the in-pipe moving apparatus 1 is rotated by about 180 degrees from the state shown in FIG. 20A). The attitude of the in-pipe moving apparatus 1 is thus finally rotated about by 180 degrees, as shown in FIG. 22B.

As a result, among the tire-integrated wheels 7 to 7 of the three sets of tire-integrated wheel units 2A to 2C, the tire-integrated wheels 7, 7 of the first and third tire-integrated wheel units are pressed against the inner-side inner surface of the T junction 62 of the pipe 60, and the tire-integrated wheel 7 of the second tire-integrated wheel unit is pressed against the outer-side inner surface of the T junction 62, as shown in FIG. 22C. The in-pipe moving apparatus 1 can therefore enter the bifurcating passage 63, as described above.

FIGS. 23A to 23C to FIGS. 24A to 24C describe action of the in-pipe moving apparatus 1 in which the in-pipe moving apparatus 1 that travels in an attitude in which the shafts of the tire-integrated wheels are maintained vertical enters a bifurcating passage 63 from a T junction 62, which is a horizontally branched segment of a pipe 60. The same description applies to a case where the bifurcating passage 63 extends upward in the vertical direction. In this state, since all the tire-integrated wheels 7 to 7 of the three sets of tire-integrated wheel units 2A to 2C are in contact with the upper inner surface or the lower inner surface perpendicular to the direction of the bifurcating passage 63, the in-pipe moving apparatus 1 cannot enter the bifurcating passage 63 even when the in-pipe moving apparatus 1 is caused to move straight in the same attitude. Therefore, also in this case, the attitude of the in-pipe moving apparatus 1 needs to be controlled at a point a predetermined distance before the in-pipe moving apparatus 1 enters the bifurcating passage 63 in such a way that the tire-integrated wheels 7, 7 of the first and third tire-integrated wheel units are pressed against the inner-side inner side surface of the bifurcating passage 63 and the tire-integrated wheel 7 of the second tire-integrated wheel unit is pressed against the outer-side inner side surface of the bifurcating passage 63.

Figure 23A:
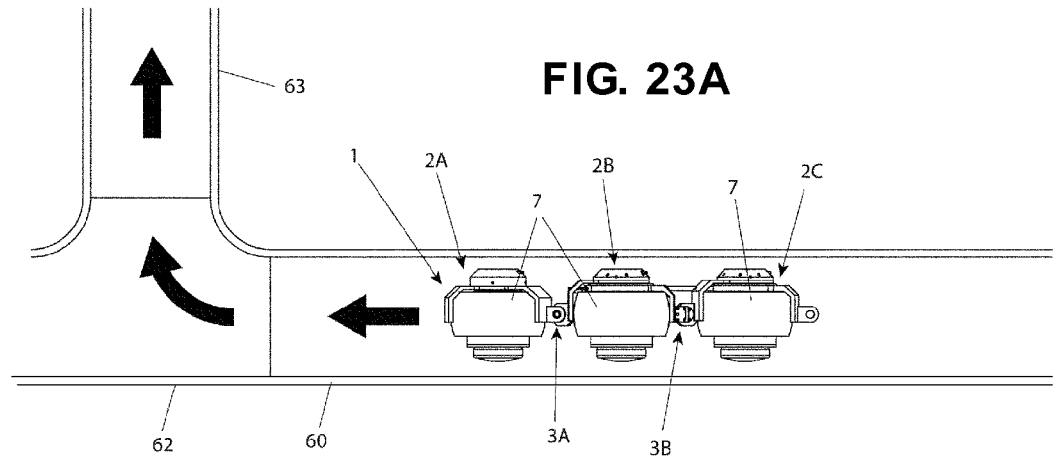
FIGS. 23A to 23C describe action of the in-pipe moving apparatus shown in FIG. 1 in which the in-pipe moving apparatus enters a bifurcating passage from a T junction of a pipe by changing the attitude of the apparatus from the vertical attitude to the horizontal attitude, FIG. 23A being a plan view of a state in which the three sets of tire-integrated wheel units move straight in the vertical direction, FIG. 23B being a plan view of a state in which the tire-integrated wheels of the three sets of tire-integrated wheel units are driven at different speeds so that a horizontally zigzag shape of the in-pipe moving apparatus is achieved, and FIG. 23C being a plan view of a state in which the tire-integrated wheels of the three sets of tire-integrated wheel units are inclined by about 30 degrees.

First, at a point a predetermined distance before the in-pipe moving apparatus 1 reaches the T junction 62, the operator operates the controller 53 to set the three motors 5 to 5 of the three sets of tire-integrated wheel units 2A to 2C at different numbers of revolutions under the control of the control device 51, as shown in FIG. 23A, as described above. The number of revolutions of the tire-integrated wheel 7 of the second tire-integrated wheel unit 2B (N2) is set to be greater than the number of revolutions of the tire-integrated wheel 7 of the first tire-integrated wheel unit 2A (N1), and the number of revolutions of the tire-integrated wheel 7 of the third tire-integrated wheel unit 2C (N3) is set to be greater than the number of revolutions of the tire-integrated wheel 7 of the second tire-integrated wheel unit 2B (N2) (N1<N2<N3).

Figure 23B:
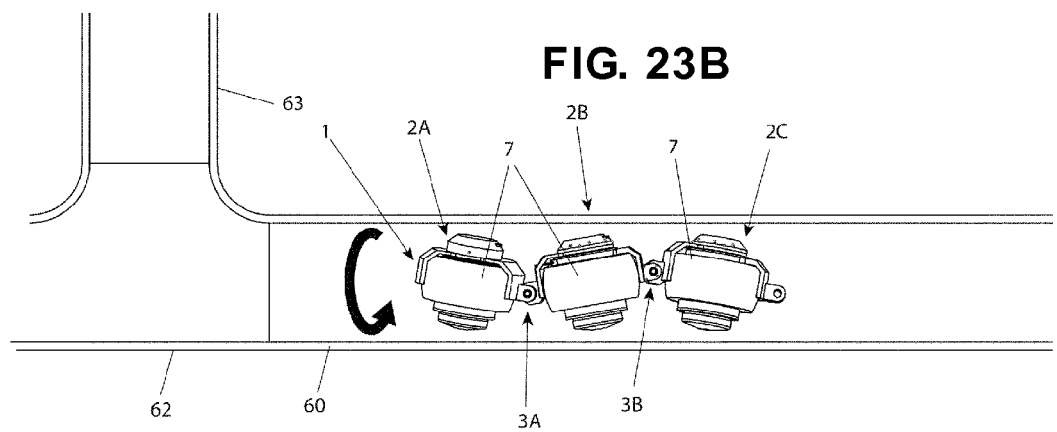
Figure 23C:
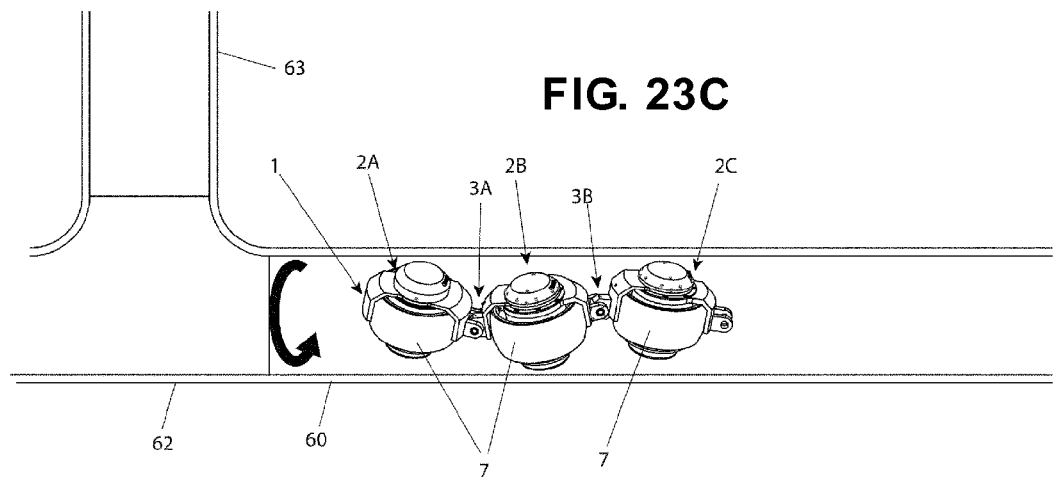
Figure 24A:
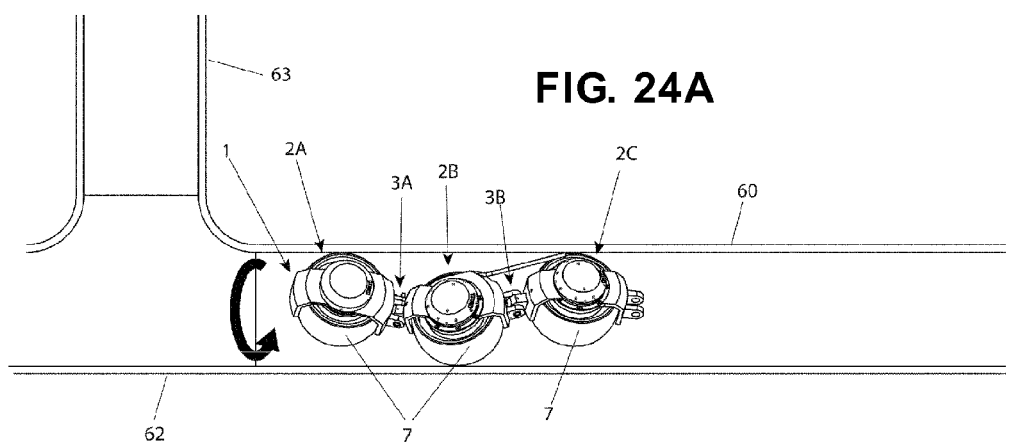
FIGS. 24A to 24C describe the action of the in-pipe moving apparatus shown in FIG. 1 in which the in-pipe moving apparatus enters a bifurcating passage from a T junction of a pipe by changing the attitude of the apparatus from the vertical attitude to the horizontal attitude, FIG. 24A being a plan view of a state in which the tire-integrated wheels of the three sets of tire-integrated wheel units are inclined by about 60 degrees, FIG. 24B being a plan view of a state in which the tire-integrated wheels of the three sets of tire-integrated wheel units are inclined by about 90 degrees so that a zigzag attitude is achieved, and FIG. 24C being a plan view of a state in which the attitude of the tire-integrated wheels of the three sets of tire-integrated wheel units is changed from the zigzag attitude to the horizontal attitude.
Figure 24B:
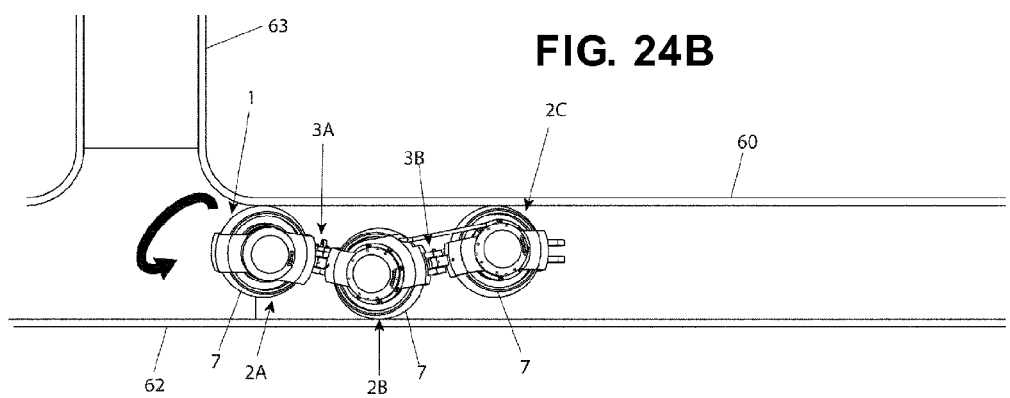

As a result, since the number of revolutions of the tire-integrated wheel 7 located behind is greater than the number of revolutions of the tire-integrated wheel 7 located ahead, a state in which the three tire-integrated wheels 7 to 7 approach each other occurs, as shown in FIG. 23B, and the state sequentially transitions to the following states: the state shown in FIG. 23C (state in which the in-pipe moving apparatus 1 is rotated by about 30 degrees from the state shown in FIG. 23B); the state shown in FIG. 24A (state in which the in-pipe moving apparatus 1 is rotated by about 60 degrees from the state shown in FIG. 23B); and the state shown in FIG. 24B (state in which the in-pipe moving apparatus 1 is rotated by about 90 degrees from the state shown in FIG. 23B). The attitude of the in-pipe moving apparatus 1 is thus rotated about by 90 degrees, as shown in FIG. 24B.

Figure 24C:
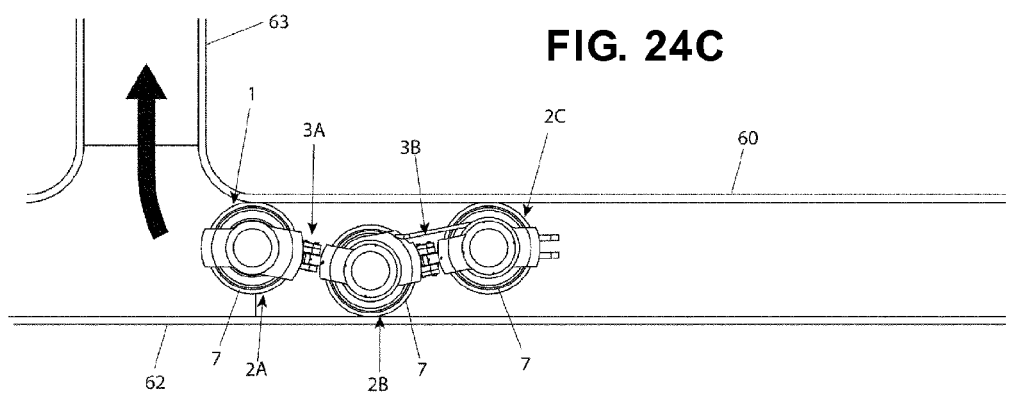

As a result, among the tire-integrated wheels 7 to 7 of the three sets of tire-integrated wheel units 2A to 2C, the tire-integrated wheels 7, 7 of the first and third tire-integrated wheel units are pressed against the inner-side inner surface of the T junction 62 of the pipe 60, and the tire-integrated wheel 7 of the second tire-integrated wheel unit is pressed against the outer-side inner surface of the bifurcating passage 63, as shown in FIG. 24C. The in-pipe moving apparatus 1 can therefore enter the bifurcating passage 63, as described above.

According to the present example, the in-pipe moving apparatus 1 is allowed not only, of course, to travel straight along a linear segment of the pipe 60 but also to smoothly enter the bent segment (T-shaped curve) 65, a T junction, crossed passages, and other nonlinear passages irrespective of the attitude (vertical attitude or horizontal attitude) of the in-pipe moving apparatus 1 with no change of the attitude of the in-pipe moving apparatus 1 or with simple attitude control thereof.

Figure 25:
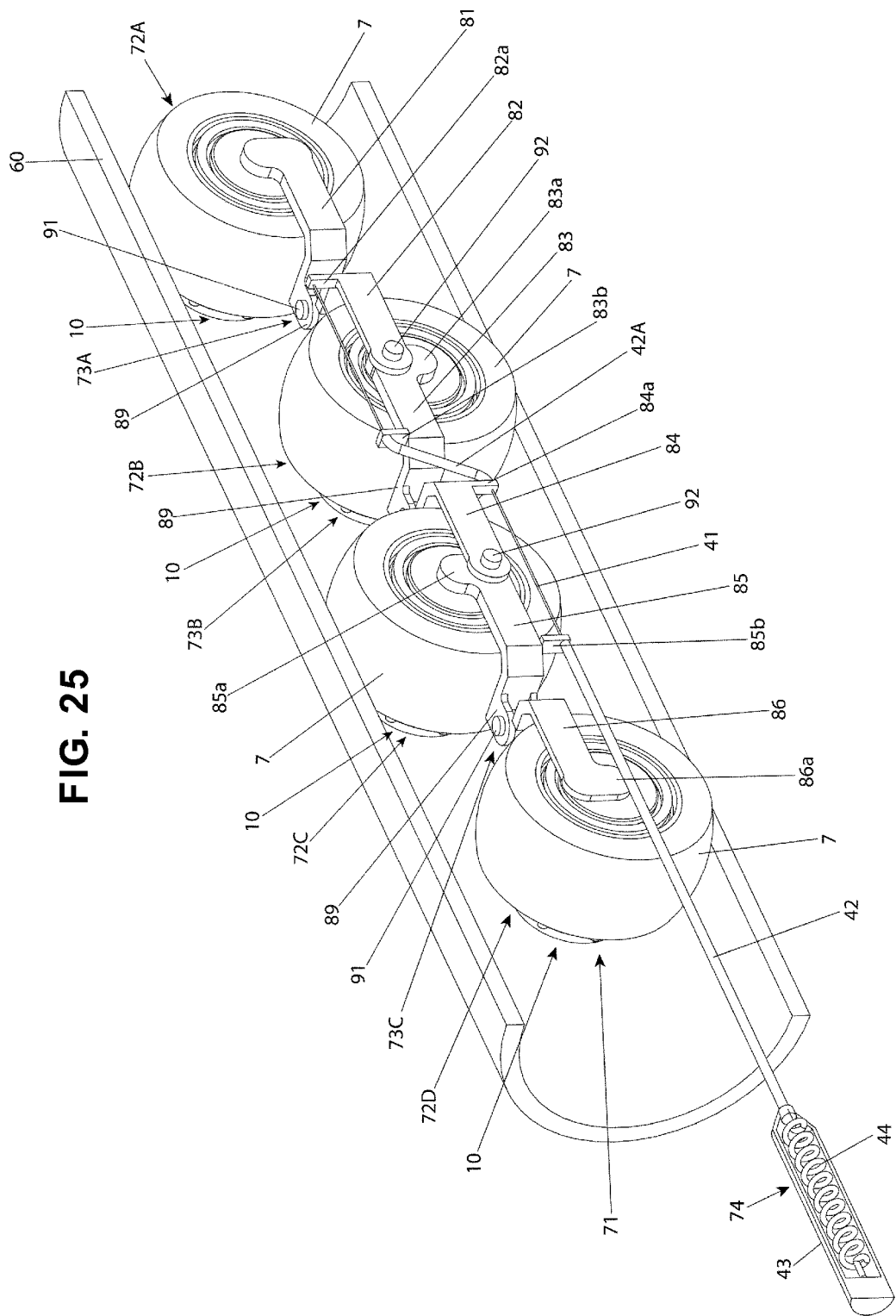
FIG. 25 is an exterior appearance perspective view showing a second embodiment of the in-pipe moving apparatus according to the invention.

FIG. 25 shows a second embodiment of the in-pipe moving apparatus according to the invention. An in-pipe moving apparatus 71 according to the second embodiment includes four sets of tire-integrated wheel units 72A, 72B, 72C, and 72D; three sets of joint sections 73A, 73B, and 73C, which pivotably link the adjacent tire-integrated wheel units 72A and 72B to each other, the adjacent tire-integrated wheel units 72B and 72C to each other, and the adjacent tire-integrated wheel units 72C and 72D to each other; a tension imparting member 74, which is a first example of a bending generator that imparts tension for achieving a zigzag arrangement of the four sets of tire-integrated wheel units 72A to 72D disposed in series with shafts of the tire-integrated wheels oriented in the horizontal direction; and other components.

One side section of a first frame 81 is fixed to the rotary shaft of the drive section 10 in the first tire-integrated wheel unit 72A. The first frame 81 is bent in an L-like shape, and the other other-side section of the first frame 81 is provided with a pair of first joint pieces 89, which protrude in the direction opposite the direction in which the one-side section extends. Each of the pair of first joint pieces 89 is provided with an insertion hole that passes therethrough in a direction roughly perpendicular to the axial center line of the rotary shaft.

One side section of a first frame 83 is fixed to the rotary shaft of the drive section 10 in the second tire-integrated wheel unit 72B. The first frame 83 is bent in an L-like shape, and the other side section of the first frame 83 is provided with a pair of first joint pieces 89, which protrude in the direction opposite the direction in which the one-side section extends. Each of the pair of first joint pieces 89 is provided with an insertion hole that passes therethrough in a direction roughly perpendicular to the axial center line of the rotary shaft. A bent section of the first frame 83 forms a cable support piece 83b, which protrudes in the direction opposite a bearing section 83a.

One side section of a second frame 82 is pivotably linked to the one-side section of the first frame 83. The second frame 82 is formed of a member bent in an L-like shape, and the other side section of the second frame 82 is provided with a second joint piece that protrudes in the direction opposite the direction in which the one side section extends. The second joint piece is provided with an insertion hole that passes therethrough in a direction roughly perpendicular to the direction of the axial center line of the rotary shaft. Further, a bent portion of the second frame 82 forms a cable support piece 82a.

The pair of first joint pieces 89 of the first frame 81, the second joint piece of the second frame 82, and a pivotal shaft 91 form the first joint section 73A. That is, the second joint piece is interposed between the pair of first joint pieces 89, and the pivotal shaft 91 is inserted through the insertion holes provided in the first joint pieces 89 and the second joint piece. The first frame 81 and the second frame 82 are thus linked to each other in a freely swingable manner in the horizontal direction, which is perpendicular to a longitudinal cross section of the tire-integrated wheels 7.

One side section of a first frame 85 is fixed to the rotary shaft of the drive section 10 in the third tire-integrated wheel unit 72C. The first frame 85 is bent in an L-like shape, and the other side section of the first frame 85 is provided with a pair of first joint pieces 89, which protrude in the direction opposite the direction in which the one side section extends. Each of the pair of first joint pieces 89 is provided with an insertion hole that passes therethrough in a direction roughly perpendicular to the axial center line of the rotary shaft. A bent portion of the first frame 85 forms a cable support piece 85b, which protrudes in the direction opposite a bearing section 85a.

One side portion of a second frame 84 is pivotably linked to the one-side section of the first frame 85. The second frame 84 is formed of a member bent in an L-like shape, and the other side section of the second frame 84 is provided with a second joint piece that protrudes in the direction opposite the direction in which the one side section extends. The second joint piece is provided with an insertion hole that passes therethrough in a direction roughly perpendicular to the axial center line of the rotary shaft. Further, a bent portion of the second frame 84 forms a cable support piece 84a.

The pair of first joint pieces 89 of the first frame 83, the second joint piece of the second frame 84, and a pivotal shaft 91 form the second joint section 73B. That is, the second joint piece is interposed between the pair of first joint pieces 89, and the pivotal shaft 91 is inserted through the insertion holes provided in the first joint pieces 89 and the second joint piece. The first frame 83 and the second frame 84 are thus linked to each other in a swingable manner in the horizontal direction, which is perpendicular to a longitudinal cross section of the tire-integrated wheels 7.

Further, a one-side section of a second frame 86 is fixed to the rotary shaft of the drive section 10 in the fourth tire-integrated wheel unit 72D. The second frame 86 is formed of a member bent in an L-like shape, and an other-side section of the second frame 86 is provided with a second joint piece that protrudes in the direction opposite the direction in which the one-side section extends. The second joint piece is provided with an insertion hole that passes therethrough in a direction roughly perpendicular to the axial center line of the rotary shaft.

The second joint piece of the second frame 86, the pair of first joint pieces 89 of the first frame 85, and a pivotal shaft 91 form the third joint section 73C. That is, the second joint piece is interposed between the pair of first joint pieces 89, and the pivotal shaft 91 is inserted through the insertion holes provided in the first joint pieces 89 and the second joint piece. The first frame 85 and the second frame 86 are thus linked to each other in a swingable manner in the horizontal direction, which is perpendicular to a longitudinal cross section of the tire-integrated wheels 7.

The four sets of tire-integrated wheel units 71A to 72D are thus arranged in a zigzag shape (alternately) in the upward/downward direction. In the four sets of tire-integrated wheel units 71A to 72D swingably linked to each other, a tension adjustment mechanism 74, which is a first example of the bending generator, installed across the segment from the second tire-integrated wheel unit 72B to the third tire-integrated wheel unit 72C. The tension adjustment mechanism 74 is pulled with appropriate tensile force as an initial setting.

The tension adjustment mechanism 74 has the same configuration as that described in the embodiment described above and is formed of the cable 41, the tube 42, the case 43, and the coil spring 44. The front end of the tube 42 is fixed to the cable support piece 85b provided on the first frame 85. The front portion of the cable 41 that protrudes through the tube 42 passes through the cable support piece 84a provided on the second frame 84 and a tube piece 42A provided between the second frame 84 and the first frame 83, and the front end 41a of the cable is fixed to the cable support piece 82a provided on the second frame 82.

In this case, the cable support piece 82a of the second frame 82 and the cable support piece 83b of the first frame 83 in the second tire-integrated wheel unit 72B are present above the rotary shaft of the tire-integrated wheel of the second tire-integrated wheel unit 72B. In contrast, the cable support piece 84a of the second frame 84 and the cable support piece 85b of the first frame 85 in the third tire-integrated wheel unit 72C are present below the rotary shaft of the tire-integrated wheel of the third tire-integrated wheel unit 72C.

In this configuration, the spring force produced by the coil spring urges the first tire-integrated wheel unit 72A and the third tire-integrated wheel unit 73C in the same direction and the second tire-integrated wheel unit 72B and the fourth tire-integrated wheel unit 72D in the opposite direction. Further, since the tube piece 42A is present between the cable support piece 83b and the cable support piece 84a, traction force acting on the cable 41 does not produce unnecessary pivotal motion around the pivotal shaft 91 between the tire-integrated wheel units corresponding to the tube piece 42A.

According to the configuration of the present embodiment, the tension adjustment mechanism 74 formed of a single spring and provided external to the tire-integrated wheel train of the in-pipe moving apparatus 71 is characterized by an ability to produce torque that bends a plurality of tire-integrated wheel units, that is, the tire-integrated wheel units 72B and 72C. As a result, also in the present embodiment, the in-pipe moving apparatus 71 is allowed not only, of course, to travel straight along a linear segment of the pipe 60 but also to smoothly enter the curved segment, a T junction, a bifurcating passage, and other nonlinear passages irrespective of the attitude (vertical attitude or horizontal attitude) of the in-pipe moving apparatus with simple attitude control thereof. Further, since the number of power sections formed of the motors 5 is increased to four, increasing the number of tire-integrated wheel units allows an increase in force that drives the in-pipe moving apparatus 71 in accordance with the increase in the number of tire-integrated wheel units.

Figure 26A:
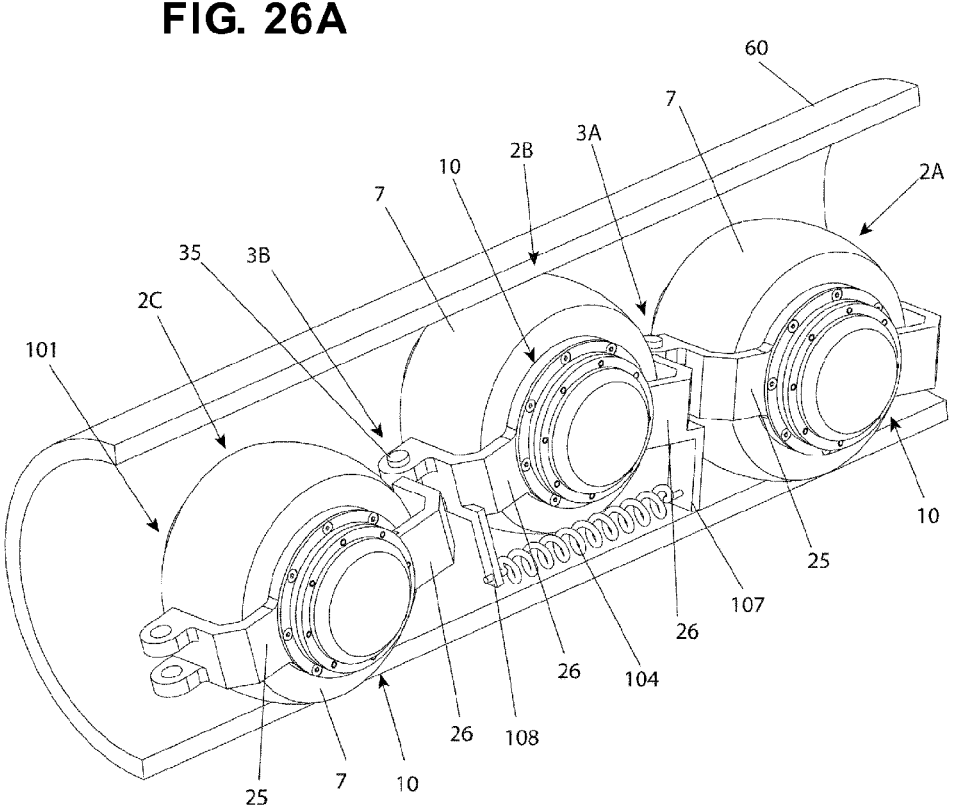
FIGS. 26A and 26B show exterior appearance of a third embodiment of the in-pipe moving apparatus according to the invention, FIG. 26A being a perspective view and FIG. 26B being a side view.
Figure 26B:
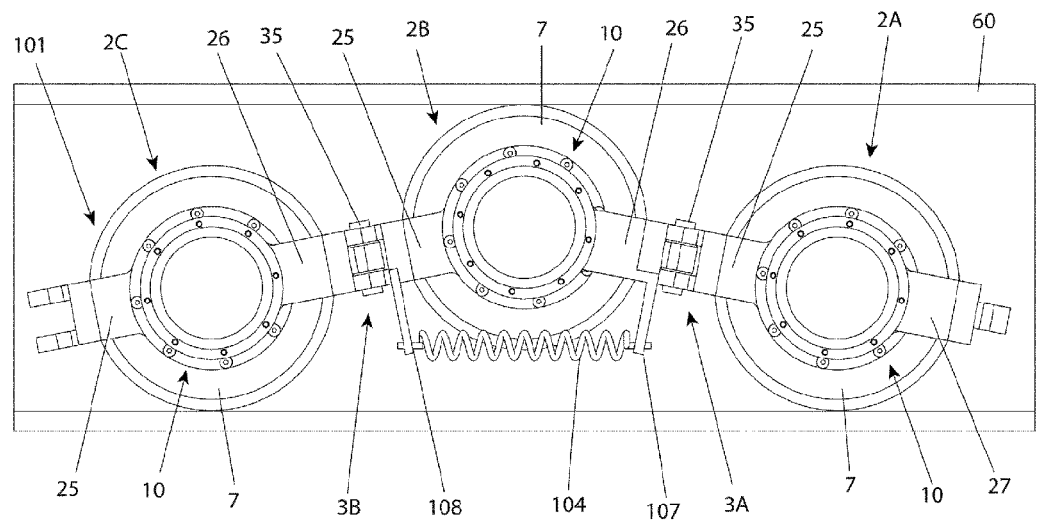

FIGS. 26A and 26B show a third embodiment of the in-pipe moving apparatus according to the invention. An in-pipe moving apparatus 101 according to the third embodiment differs from in-pipe moving apparatus 1 according to the first embodiment shown in FIG. 1 and other figures in that the bending generator is formed only of a coil spring 104. Therefore, the following description will be made only of the coil spring 104 and portions associated therewith, and the other same portions as those in the first embodiment have the same reference characters and will not be described.

The in-pipe moving apparatus 101 includes the three sets of tire-integrated wheel units 2A, 2B, and 2C, the two sets of joint sections 3A and 3B, and the coil spring 104. One of the second frames 25 is fixed to the first tire-integrated wheel unit 2A on a freely rotatable manner, and the fixed frame 27 is fixed to the drive section 10 in the tire-integrated wheel unit 2A. Another one of the second frames 25 is attached to the second tire-integrated wheel unit 2B in a freely pivotable manner, and one of the first frames 26 is fixed to the drive section 10 in the tire-integrated wheel unit 2B. The other one of the first frames 26 is fixed to the drive section 10 in the third tire-integrated wheel unit 2C, and the other one of the second frames 25 is attached to the third tire-integrated wheel unit in a freely pivotable manner. The coil spring 104 is attached in association with the second tire-integrated wheel unit 2B. Therefore, the second frame 25 in the tire-integrated wheel unit 2B is provided with a second spring reception piece 108, and the first frame 26 in the tire-integrated wheel unit 2B is provided with a first spring reception piece 107. The coil spring 104, which is installed between the first spring reception piece 107 and the second spring reception piece 108, imparts tensile force that causes the second frame 25 and the first frame 26 in the tire-integrated wheel unit 2B to be attracted to each other.

According to the third embodiment, in which the tension imparting member is formed only of the coil spring 104, the configuration of the in-pipe moving apparatus 101 can be simplified. Further, the coil spring 104 also allows the in-pipe moving apparatus 101 to perform the same action as that of the in-pipe moving apparatus 1 according to the first embodiment and further provides advantageous effects of reduction in the number of parts and reduction in manufacturing cost. The coil spring 104 may instead be a torsion spring, a plate spring, or any other type of spring.

Figure 27:
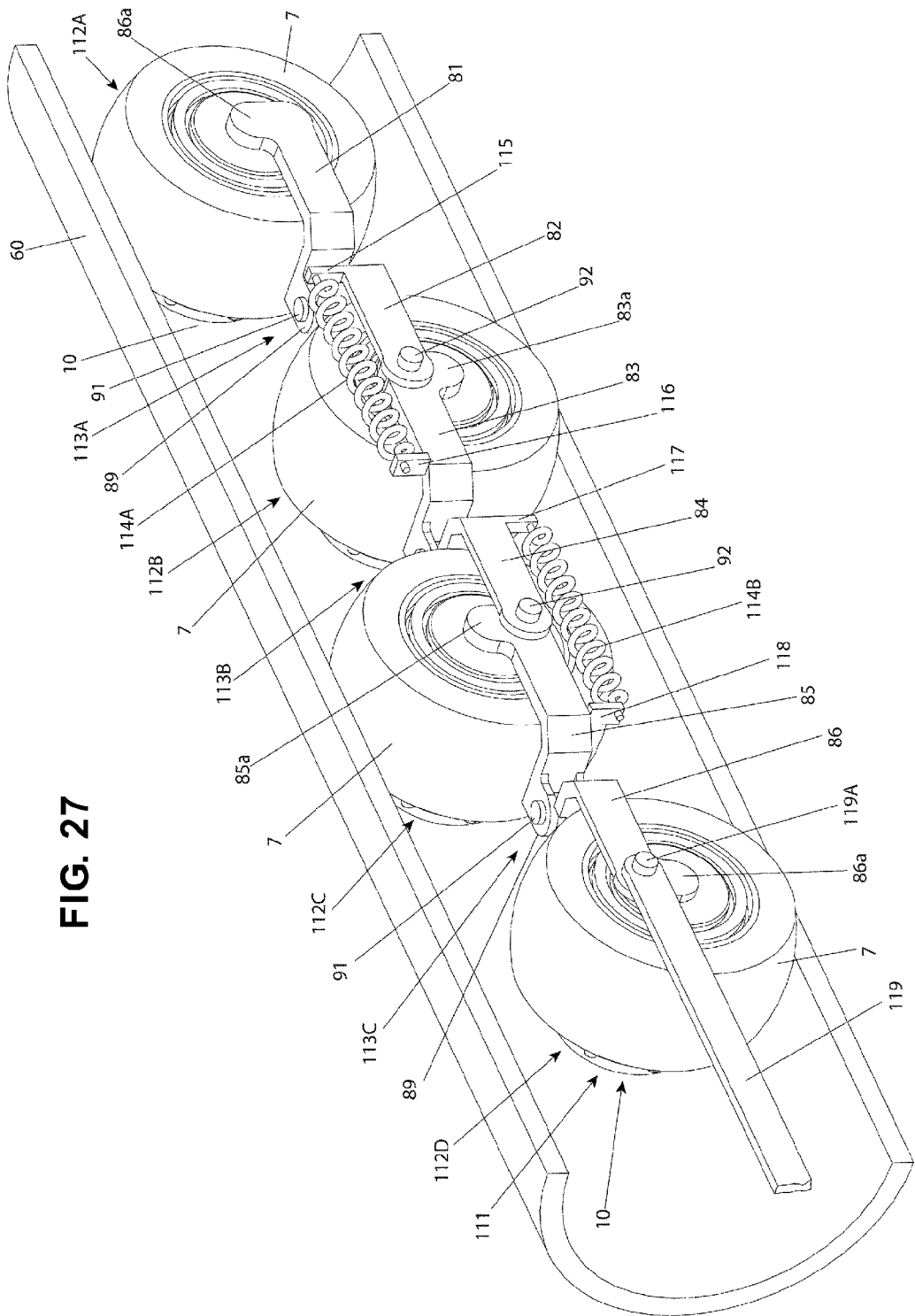
FIG. 27 is an exterior appearance perspective view showing a fourth embodiment of the in-pipe moving apparatus according to the invention.

FIG. 27 shows a fourth embodiment of the in-pipe moving apparatus according to the invention. An in-pipe moving apparatus 111 according to the fourth embodiment differs from the in-pipe moving apparatus 71 according to the second embodiment shown in FIG. 25 in that the tension adjustment mechanism 74 is replaced with two coil springs 114A and 114B. Therefore, the following description will be made only of the coil springs 114A and 114B and portions associated therewith, and the other same portions as those in the second embodiment have the same reference characters and will not be described.

The second frame 82 and the first frame 83 in a second tire-integrated wheel unit 112B are provided with spring reception pieces 115 and 116, which face each other and protrude from one side of the second frame 82 and the first frame 83 in the same direction, and the first coil spring 114A is installed between the spring reception pieces 115 and 116. Further, the second frame 84 and the first frame 85 in a third tire-integrated wheel unit 112C are provided with spring reception pieces 117 and 118, which face each other and protrude from one side of the second frame 84 and the first frame 85 in the same direction but on the side opposite the spring reception pieces 115 and 116, and the second coil spring 114B is installed between the spring reception pieces 117 and 118. The configuration described above also allows the four sets of tire-integrated wheel units 112A to 112D to be arranged in a zigzag shape and in a swingable manner in the direction perpendicular to the axial direction of the rotary shafts of the drive sections 10.

According to the fourth embodiment, in which the tension imparting member is formed only of the two coil springs 114A and 114B, the configuration of the in-pipe moving apparatus 111 can be simplified. Further, the coil springs 114A and 114B also allow the in-pipe moving apparatus 111 to perform the same action as that of the in-pipe moving apparatus 71 according to the second embodiment and further provide advantageous effects of reduction in the number of parts and reduction in manufacturing cost. Moreover, since the number of drive sections 10 including the motors 5 is increased to four, increasing the number of tire-integrated wheel units allows an increase in force that drives the in-pipe moving apparatus 111 in accordance with the increase in the number of tire-integrated wheel units. The number of tire-integrated wheel units is not limited to three or four in the embodiments described above, and five or more tire-integrated wheel units can, of course, be linked to each other to form an in-pipe moving apparatus. Reference number 119 denotes a guide frame that guides lead wires extracted from the drive sections 10 in the tire-integrated wheel units 112A to 112D. One end of the guide frame 119 is pivotably attached to the second frame 86 via a support shaft 119A.

Figure 28A:
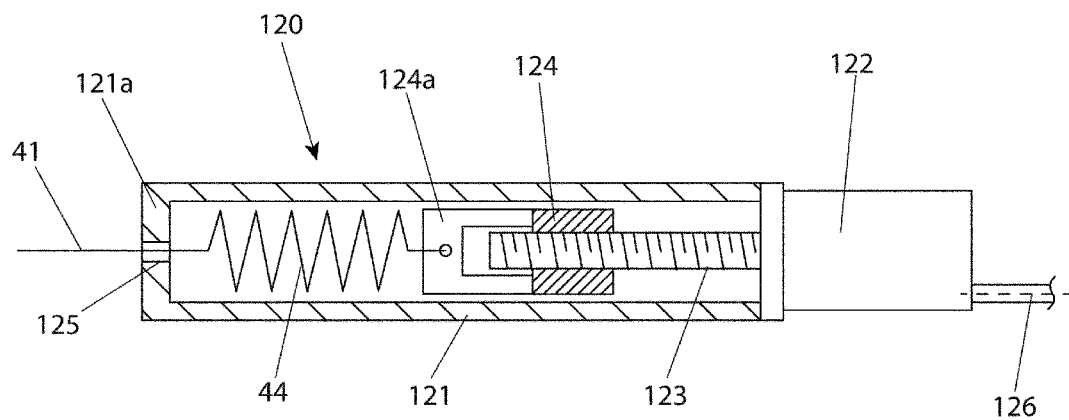
FIGS. 28A and 28B show other examples of a bending generator according to any of the in-pipe moving apparatus of the invention, FIG. 28A being a descriptive diagram schematically showing the configuration of a second example of the bending generator and FIG. 28B being a descriptive diagram schematically showing the configuration of a third example of the bending generator.

FIG. 28A shows a third example of the bending generator according to any of the in-pipe moving apparatus of the invention. A bending generator 120 shown in the present example is configured to be capable of adjusting a vehicle length determined by the magnitude of the V-shaped angle of the in-pipe moving apparatus or a vehicle length determined by the magnitude of the zigzag angle of the in-pipe moving apparatus by changing the magnitude of tensile force produced by the coil spring. The bending generator 102 includes the coil spring 44, a case 121, a motor 122, a nut 124, and other components.

The case 121 of the bending generator 120 is formed of a member having a bottomed tubular shape with one closed end, and the tubular case preferably has a rectangular, hexagonal, octagonal, triangular, or any other polygonal cross-sectional shape, an elliptical cross-sectional shape, or any other suitable cross-sectional shape that prevents the nut 124 from rotating. Since a purpose in using the case 121 having any of the shapes described above is prevention of rotation of the nut 124 on the basis of the shape of the case, a cylindrical case can also be used as long as some means other than the shape of the case can prevent the nut 124 from rotating. An example of the means for preventing the nut 124 from rotating may be a configuration in which the case is provided with a protrusion, such as a pin and a key, and the nut is provided with a key groove that slidably engages with the protrusion.

The motor 122, which has a rotary shaft 123 inserted into the interior of the case 121, is fixed to an opening-side end of the case 121 with fixing means that is not shown, such as fixing screws. The rotary shaft 123 is provided with a male thread along a roughly entire length thereof, and the threaded portion is screwed into the nut 124. The nut 124 is provided with an arm 124a, which protrudes toward one side, and one end of the coil spring 44 is locked to a front end portion of the arm 124a. The cable 41 is linked to the other end of the coil spring 44, and the cable 41 passes through a hole 125 provided at the center of an end surface 121a of the case 121 and exits out thereof. The motor 122 is connected to a controller (controller 53 in FIG. 6B) via a lead wire 126 and driven and controlled through operation of the controller 53.

According to the bending generator 120, driving the motor 122 to rotate the rotary shaft 123 so as to move the nut 124 away from the motor 122 allows the coil spring 44 to loosen and therefore the spring force to decrease, whereby the bent angle of the in-pipe moving apparatus is reduced for an increase in the vehicle length. Conversely, driving the motor 122 to rotate the rotary shaft 123 so as to move the nut 124 toward the motor 122 allows the coil spring 44 to tighten and therefore the spring force to increase, whereby the bent angle of the in-pipe moving apparatus is increased for a decrease in the vehicle length.

Figure 28B:
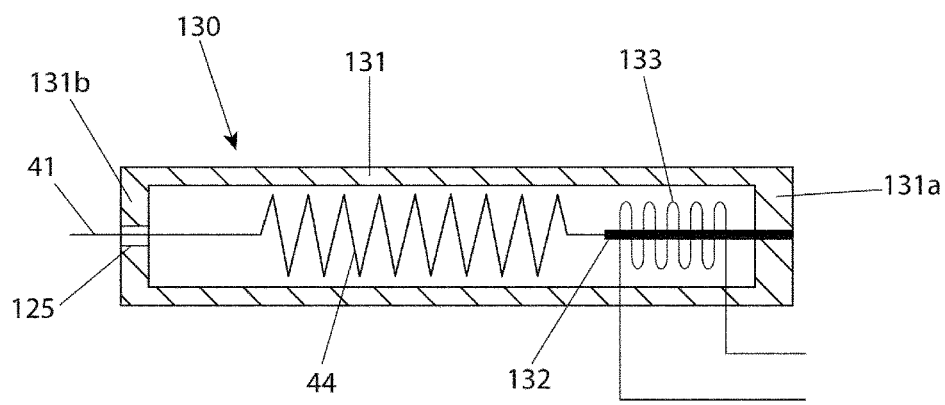

FIG. 28B shows a fourth example of the bending generator according to any of the in-pipe moving apparatus of the invention. A bending generator 130 shown in the present example is so configured that when the in-pipe moving apparatus malfunctions, a fiber piece 132, which supports one end of the coil spring 44, is burned out with a heater 133 to nullify the tensile force produced by the coil spring 44 so that the in-pipe moving apparatus has a linear shape and can therefore be readily taken out of a pipe. The bending generator 130 includes the coil spring 44, a case 131, the fiber piece 132, the heater 133, and other components.

The case 131 of the bending generator 130 is formed of a member having a bottomed tubular shape with closed ends, and one end of the fiber piece 132 is fixed to one end surface 131a of the case 131. The coil spring 44 is linked to the other end of the fiber piece 132, and the cable 41 is linked to the other end of the coil spring 44, passes through a hole 125 provided at the center of the other end surface 131b of the case 131, and exits out thereof. The heater 133 is wound around the fiber piece 132. The heater 133 is connected to a controller (controller 53 in FIG. 6B) and driven and controlled through operation of the controller 53.

According to the bending generator 130, when the in-pipe moving apparatus malfunctions in a pipe and cannot travel by itself, the in-pipe moving apparatus can be readily taken out of the pipe by cutting the fiber piece 132. For example, when the in-pipe moving apparatus malfunctions in a pipe and cannot travel by itself, the spring force produced by the coil spring 44 presses the tire-integrated wheels 7 against the inner surface of the pipe, and it is therefore difficult to take the in-pipe moving apparatus out of the pipe. In this case, electric power is supplied to the heater 133 to burn out the fiber piece 132. When the fiber piece 132 is burned out, the one end of the coil spring 44 becomes a free end, the tensile force produced by the coil spring 44 is nullified. As a result, since the tensile force that causes the in-pipe moving apparatus to have a V-like shape (or a zigzag shape) is removed, the in-pipe moving apparatus is allowed to have a linear shape. Since no force therefore presses the tire-integrated wheels 7 against the inner surface of the pipe, the in-pipe moving apparatus can be readily taken out of the pipe.

The invention has been described above but is not limited to the embodiments described above, and a variety of variations are conceivable under the doctrine of equivalents. A person skilled in the art would easily understand that a variety of changes can be made to the embodiments within the scope of the invention set forth in the claims.

The invention claimed is:

1. An in-pipe moving apparatus characterized in that:
   the in-pipe traveling apparatus comprises at least three sets of tire-integrated wheel units arranged in series in a traveling direction;
   at least two sets of joint sections that pivotably link the at least three sets of tire-integrated wheel units to each other;
   at least one set of tire-integrated wheel units of the three sets of tire-integrated wheel units includes a tire-integrated wheel, a drive section that drives and rotates the tire-integrated wheel, a first frame fixed to the drive section, and at least one second frame pivotably attached to the drive section or the first frame;
   a bending generator is provided between the first frame and the second frame in the at least one set of tire-integrated wheel units and imparts tension for causing the first frame and the second frame to have a V-like bent shape;
   each of the two sets of joint sections is configured to be pivotable in a direction roughly perpendicular to the direction in which the second frames pivot;
   the first frame in the at least one set of tire-integrated wheel units is pivotably linked to the second frame in an adjacent tire-integrated wheel unit, and the second frame in the at least one set of tire-integrated wheel units is pivotably linked to the first frame in an adjacent tire-integrated wheel unit to configure the at least two sets of joint sections.

2. The in-pipe moving apparatus according to claim 1, characterized in that the tire-integrated wheel units each include a prime mover, the tire-integrated wheel pivotably linked to an output section of the prime mover on a radially outward side of the output section with a predetermined gap between the tire-integrated wheel and the output section and integrated with the output section of the prime mover, the first frame fixed to a member of the prime mover, and the second frame supported pivotably relative to the member of the prime mover, and further include the bending generator that imparts tension for causing the first frames and the second frames to have a V-like bent shape.

3. The in-pipe moving apparatus according to claim 2, characterized in that the bending generator is formed of a spring that produces force that causes the first frames and the second frames to approach each other, a spring having a cable that produces force that causes the first frames and the second frames to approach each other, or a tension adjustment mechanism that changes tension produced by a spring.

* * * * *